United States Patent
Yoon et al.

(10) Patent No.: US 11,505,557 B2
(45) Date of Patent: Nov. 22, 2022

(54) ORGANIC COMPOUND, AND ORGANIC LIGHT EMITTING DIODE AND ORGANIC LIGHT EMITTING DISPLAY DEVICE INCLUDING THE SAME

(71) Applicants: LG Display Co., Ltd., Seoul (KR); Korea University Research and Business Foundation, Seoul (KR)

(72) Inventors: Dae-Wi Yoon, Paju-si (KR); Bo-Min Seo, Paju-si (KR); Chun-Ki Kim, Paju-si (KR); Dong-Hoon Choi, Paju-si (KR); Min-Ju Cho, Paju-si (KR); Su-Na Choi, Paju-si (KR); Mallesham Godumala, Paju-si (KR)

(73) Assignees: LG DISPLAY CO., LTD., Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 395 days.

(21) Appl. No.: 16/712,291

(22) Filed: Dec. 12, 2019

(65) Prior Publication Data
US 2020/0190100 A1 Jun. 18, 2020

(30) Foreign Application Priority Data
Dec. 14, 2018 (KR) .......................... 10-2018-0161942

(51) Int. Cl.
*C07D 491/052* (2006.01)
*C07D 519/00* (2006.01)
*H01L 51/00* (2006.01)
*H01L 51/50* (2006.01)

(52) U.S. Cl.
CPC ....... *C07D 491/052* (2013.01); *C07D 519/00* (2013.01); *H01L 51/0061* (2013.01); *H01L 51/0072* (2013.01); *H01L 51/5004* (2013.01)

(58) Field of Classification Search
None
See application file for complete search history.

(56) References Cited

U.S. PATENT DOCUMENTS

2003/0129449 A1* 7/2003 Parton .................. H01L 51/006
564/429
2006/0063034 A1 3/2006 Chen et al.
(Continued)

FOREIGN PATENT DOCUMENTS

WO WO-2016/045769 A1 3/2016

OTHER PUBLICATIONS

Godumala et al. (Chem. Mater. 2018, 30, 5005-5012).*
(Continued)

*Primary Examiner* — Jay Yang
(74) *Attorney, Agent, or Firm* — Birch, Stewart, Kolasch & Birch, LLP

(57) ABSTRACT

Discussed is an organic compound of Formula 1 and an organic light emitting diode and an OLED device including the organic compound. In the organic compound, Ar1 is a heteroaryl group comprising a nitrogen atom, and Ar2 is a $C_6$ to $C_{30}$ aryl group, and R is a $C_1$ to $C_{10}$ alkyl group. The organic compound may be included in an emitting material layer of the organic light emitting diode as a host such that an emitting efficiency and a lifespan of the organic light emitting diode and the OLED device are improved.

Formula 1

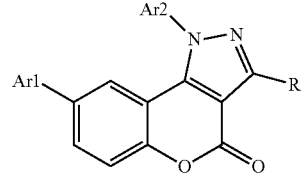

20 Claims, 7 Drawing Sheets

(56) References Cited

U.S. PATENT DOCUMENTS

2006/0113905 A1* 6/2006 Nakamura .......... H01L 27/3244
                                                    313/511
2008/0157663 A1* 7/2008 Sung .................. H01L 51/5234
                                                    445/24

OTHER PUBLICATIONS

Uoyama et al., "Highly efficient organic light-emitting diodes from delayed fluorescence", Nature 2012, vol. 492, pp. 234-238. Total 7 pages.

Jihua et al., "Progress on Donor-Acceptor Type Thermally Activated Delayed Fluorescence Based Blue Emitters," Chinese Journal of Organic Chemistry, vol. 37, 2017 (Published online Jun. 16, 2017). pp. 2457-2480 (24 pages total), with English abstract.

Nagaraj et al., "Rapid and Efficient Microwave Assisted Method for the Regioselective Synthesis of 8,8'-Methylene-bis-4-oxo-1H and 2H-chromeno[4,3-c]pyrazoles," Journal of Heterocyclic Chemistry, vol. 44, No. 6, Nov.-Dec. 2007, pp. 1357-1361 (5 pages total).

* cited by examiner

100

ORGANIC COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATIONS

The present application claims the benefit of Korean Patent Application No. 10-2018-0161942 filed in the Republic of Korea on Dec. 14, 2018, which is hereby incorporated by reference in its entirety.

BACKGROUND

Field of Technology

The present disclosure relates to an organic compound, and more particularly, to an organic compound having high energy level of the triplet state, and an organic light emitting diode and an organic light emitting display (OLED) device including the organic compound.

Discussion of the Related Art

Recently, the requirements for flat panel display devices having a small occupied area has increased. Among the flat panel display devices, a technology of an OLED device, which includes an organic light emitting diode and may be called to as an organic electroluminescent device, has been rapidly developed.

The organic light emitting diode emits light by injecting electrons from a cathode as an electron injection electrode and holes from an anode as a hole injection electrode into an organic emitting layer, combining the electrons with the holes, generating an exciton, and transforming the exciton from an excited state to a ground state. A flexible transparent substrate, for example, a plastic substrate, can be used as a base substrate where elements are formed. In addition, the organic light emitting diode can be operated at a voltage (e.g., 10V or below) lower than a voltage required to operate other display devices and has low power consumption. Moreover, the light from the organic light emitting diode has excellent color purity.

Recently, a delayed fluorescent compound is used for an emitter, i.e., a dopant, in an emitting material layer (EML) of the organic emitting diode. In the delayed fluorescent compound, a triplet exciton is converted into a singlet exciton by a reverse inter-system crossing (RISC) principle such that the delayed fluorescent compound provides high emitting efficiency.

The delayed fluorescent compound may be referred to as a field activated delayed fluorescent (FADF) compound or a thermally activated delayed fluorescent (TADF) compound.

On the other hand, since the emission efficiency of the dopant is rapidly decreased by a concentration quenching problem, the EML further includes a host to prevent the above problem. To confine the exciton in the delayed fluorescent compound, the host is required to have higher energy level of triplet state than the dopant.

For example, for the delayed fluorescent compound emitting blue light, bis[2-(diphenylphosphino)-phenyl]ether oxide (DPEPO), which has relatively high energy level of triplet state, is introduced as the host. However, since DPEPO includes a phosphine oxide moiety, DPEPO has an n-type property. As a result, a recombination zone of the hole and the electron in the EML is shifted into the anode side.

On the other hand, when CBP, which has a p-type property, is used as the host, a recombination zone of the hole and the electron in the EML is shifted into the cathode side.

Namely, when the related art host material is used in the EML, the recombination zone of the hole and the electron is not located in a center of the EML such that an emitting efficiency and the lifespan of the organic light emitting diode and the OLED device are decreased.

SUMMARY

The present invention is directed to an organic compound, an organic light emitting diode and an OLED device that substantially obviate one or more of the problems associated with the limitations and disadvantages of the related conventional art.

Additional features and advantages of the invention are set forth in the description which follows, and will be apparent from the description, or evident by practice of the invention. The objectives and other advantages of the invention are realized and attained by the features described herein as well as in the appended drawings.

To achieve these and other advantages in accordance with the purpose of the embodiments of the invention, as described herein, an aspect of the invention is an organic compound of:

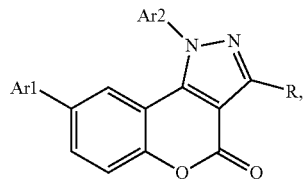

wherein Ar1 is a heteroaryl group including nitrogen atom (N), and Ar2 is a C6 to C30 aryl group, and wherein R is a C1 to C10 alkyl group.

Another aspect of the invention is an organic light emitting diode including a first electrode; a second electrode facing the first electrode; and a first emitting material layer between the first and second electrodes and including an organic compound of:

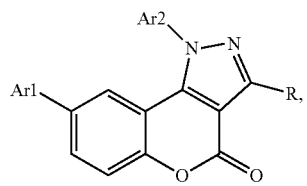

wherein Ar1 is a heteroaryl group including nitrogen atom (N), and Ar2 is a C6 to C30 aryl group, and wherein R is a C1 to C10 alkyl group.

Another aspect of the invention is an organic light emitting display device including a substrate; an organic light emitting diode disposed on the substrate, the organic light emitting diode comprising: a first electrode; a second electrode facing the first electrode; and an emitting material layer between the first and second electrodes; and a thin film transistor positioned between the substrate and the organic light emitting diode and connected to the organic light emitting diode wherein the emitting material layer includes an organic compound of Formula:

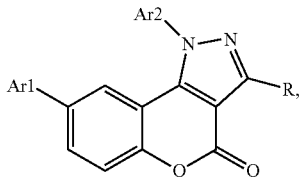

wherein Ar1 is a heteroaryl group including nitrogen atom (N), and Ar2 is a C6 to C30 aryl group, and wherein R is a C1 to C10 alkyl group.

It is to be understood that both the foregoing general description and the following detailed description are exemplary and explanatory and are intended to further explain the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION

Reference will now be made in detail to some of the examples and preferred embodiments, which are illustrated in the accompanying drawings.

Figure 1:
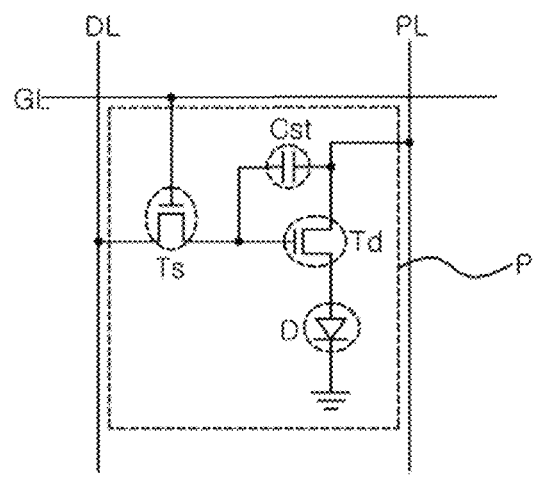
FIG. 1 is a schematic circuit diagram of an OLED device of the present disclosure.

FIG. 1 is a schematic circuit diagram of an OLED device of the present disclosure.

As shown in FIG. 1, an OLED device includes a gate line GL, a data line DL, a power line PL, a switching thin film transistor TFT Ts, a driving TFT Td, a storage capacitor Cst, and an organic light emitting diode D. The gate line GL and the data line DL cross each other to define a pixel region P.

The switching TFT Ts is connected to the gate line GL and the data line DL, and the driving TFT Td and the storage capacitor Cst are connected to the switching TFT Ts and the power line PL. The organic light emitting diode D is connected to the driving TFT Td.

In the OLED device, when the switching TFT Ts is turned on by a gate signal applied through the gate line GL, a data signal from the data line DL is applied to the gate electrode of the driving TFT Td and an electrode of the storage capacitor Cst.

When the driving TFT Td is turned on by the data signal, an electric current is supplied to the organic light emitting diode D from the power line PL. As a result, the organic light emitting diode D emits light. In this case, when the driving TFT Td is turned on, a level of an electric current applied from the power line PL to the organic light emitting diode D is determined such that the organic light emitting diode D can produce a gray scale.

The storage capacitor Cst serves to maintain the voltage of the gate electrode of the driving TFT Td when the switching TFT Ts is turned off. Accordingly, even if the switching TFT Ts is turned off, a level of an electric current applied from the power line PL to the organic light emitting diode D is maintained to next frame.

As a result, the OLED device displays a desired image.

Figure 2:
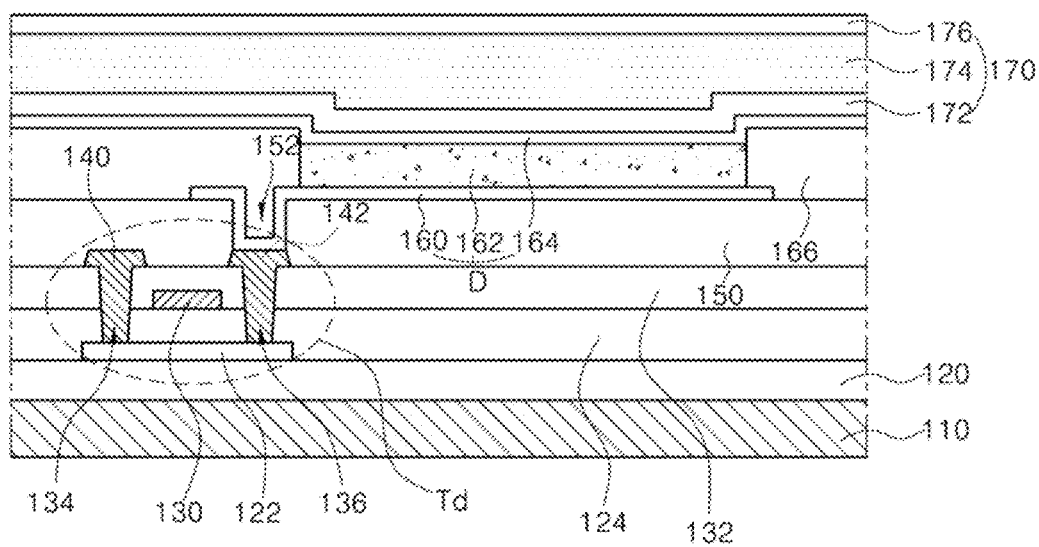
FIG. 2 is a schematic cross-sectional view of an OLED device of the present disclosure.
Figure 3:
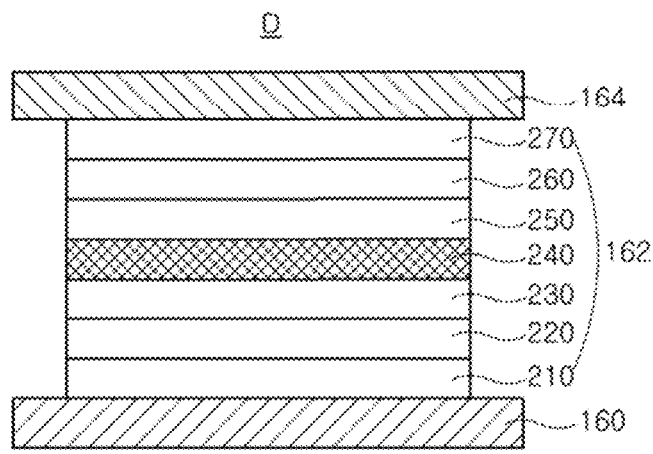
FIG. 3 is a schematic cross-sectional view of an organic light emitting diode according to a first embodiment of the present disclosure.

FIG. 2 is a schematic cross-sectional view of an OLED device of the present disclosure, and FIG. 3 is a schematic cross-sectional view of an organic light emitting diode according to a first embodiment of the present disclosure.

As shown in FIG. 2, the OLED device 100 includes a substrate 110, a driving TFT Td and an organic light emitting diode D connected to the driving TFT Td.

The substrate 110 may be a glass substrate or a plastic substrate. For example, the substrate 110 may be a polyimide substrate.

A buffer layer 120 is formed on the substrate, and the driving TFT Td is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 2, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the driving TFT Td. The driving TFT Td serves as a driving element.

In the driving TFT Td, the gate electrode 130, the source electrode 140, and the drain electrode 142 are positioned over the semiconductor layer 122. Namely, the driving TFT Td has a coplanar structure.

Alternatively, in the driving TFT Td, the gate electrode may be positioned under the semiconductor layer, and the source and drain electrodes may be positioned over the semiconductor layer such that the driving TFT Td may have an inverted staggered structure. In this instance, the semiconductor layer may include amorphous silicon.

Although not shown, the gate line and the data line cross each other to define the pixel region, and the switching TFT is formed to be connected to the gate and data lines. The switching TFT is connected to the driving TFT Td as the driving element.

In addition, the power line, which may be formed to be parallel to and spaced apart from one of the gate and data lines, and the storage capacitor for maintaining the voltage of the gate electrode of the driving TFT Td in one frame may be further formed.

A passivation layer 150, which includes a drain contact hole 152 exposing the drain electrode 142 of the driving TFT Td, is formed to cover the driving TFT Td.

A first electrode 160, which is connected to the drain electrode 142 of the driving TFT Td through the drain contact hole 152, is separately formed in each pixel region. The first electrode 160 may be an anode and may be formed of a conductive material having a relatively high work function. For example, the first electrode 160 may be formed of a transparent conductive material such as indium-tin-oxide (ITO) or indium-zinc-oxide (IZO).

When the OLED device 100 is operated in a top-emission type, a reflection electrode or a reflection layer may be formed under the first electrode 160. For example, the reflection electrode or the reflection layer may be formed of aluminum-palladium-copper (APC) alloy.

A bank layer 166 is formed on the passivation layer 150 to cover an edge of the first electrode 160. Namely, the bank layer 166 is positioned at a boundary of the pixel region and exposes a center of the first electrode 160 in the pixel region.

An organic emitting layer 162 is formed on the first electrode 160. The organic emitting layer 162 may have a single-layered structure of an emitting material layer including an emitting material. To increase an emitting efficiency of the OLED device, the organic emitting layer 162 may have a multi-layered structure.

For example, referring to FIG. 3, the organic emitting layer 162 can include an emitting material layer (EML) 240 between the first and second electrodes 160 and 164, a hole transporting layer (HTL) 220 between the first electrode 160 and the EML 240 and an electron transporting layer (ETL) 260 between the second electrode 164 and the EML 240.

In addition, the organic emitting layer 162 may further include a hole injection layer (HIL) 210 between the first electrode 160 and the HTL 220 and an electron injection layer (EIL) 270 between the second electrode 164 and the ETL 260.

Moreover, the organic emitting layer 162 may further include an electron blocking layer (EBL) 230 between the HTL 220 and the EML 240 and a hole blocking layer (HBL) 250 between the EML 240 and the ETL 260.

A second electrode 164 is formed over the substrate 110 where the organic emitting layer 162 is formed. The second electrode 164 covers an entire surface of the display area and may be formed of a conductive material having a relatively low work function to serve as a cathode. For example, the second electrode 164 may be formed of aluminum (Al), magnesium (Mg) or Al—Mg alloy.

The first electrode 160, the organic emitting layer 162 and the second electrode 164 constitute the organic light emitting diode D.

An encapsulation film 170 is formed on the second electrode 164 to prevent penetration of moisture into the organic light emitting diode D. The encapsulation film 170 includes a first inorganic insulating layer 172, an organic insulating layer 174 and a second inorganic insulating layer 176 sequentially stacked, but it is not limited thereto.

A polarization plate for reducing an ambient light reflection may be disposed over the top-emission type organic light emitting diode D. For example, the polarization plate may be a circular polarization plate.

In addition, a cover window may be attached to the encapsulation film 170 or the polarization plate. In this instance, the substrate 110 and the cover window have a flexible property such that a flexible OLED device may be provided.

The organic emitting layer 162 includes an organic compound of Formula 1.

[Formula 1]

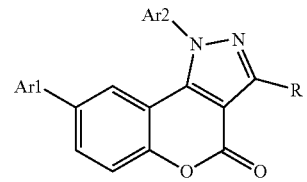

In Formula 1, Ar1 is a heteroaryl group including nitrogen atom (N), and Ar2 is a C6 to C30 aryl group. R is a C1 to C10 alkyl group.

For example, Ar1 may be represented by one of Formulas 2-1 to 2-5.

[Formula 2-1]

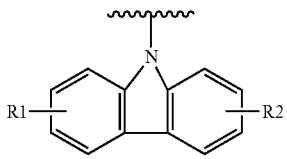

[Formula 2-2]

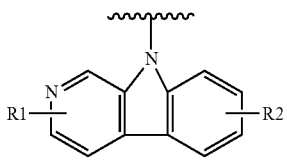

[Formula 2-3]

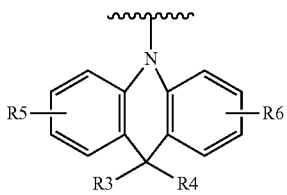

[Formula 2-4]

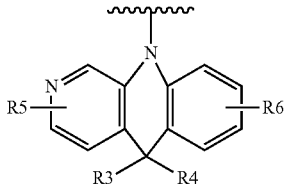

[Formula 2-5]

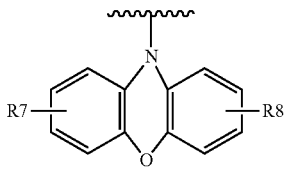

In Formulas 2-1 and 2-2, each of R1 and R2 may be independently selected from the group consisting of hydrogen, carbazole and arylamine. In Formulas 2-3 and 2-4, each of R3 and R4 may be independently selected from the group consisting of C1 to C10 alkyl and C6 to C30 aryl, or R3 and R4 may be combined (or bonded) to form a fused-ring. Each of R5 and R6 may be independently selected from the group consisting of hydrogen, carbazole and arylamine. In Formula 2-5, each of R7 and R8 may be independently selected from the group consisting of hydrogen, carbazole and arylamine.

For example, Ar1 in Formula 1 may be selected from Formula 3.

[Formula 3]

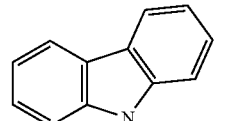

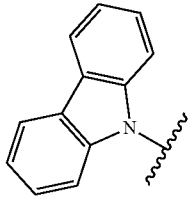

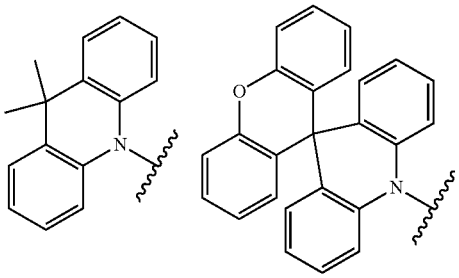

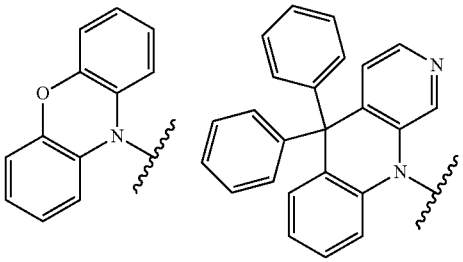

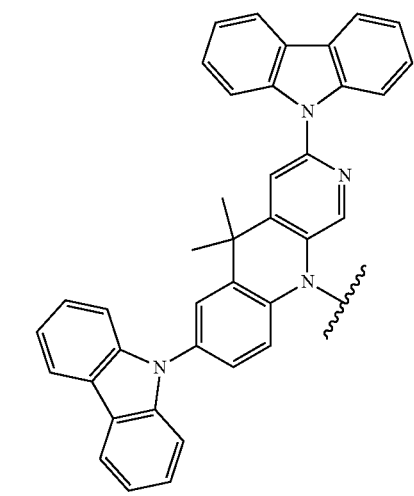
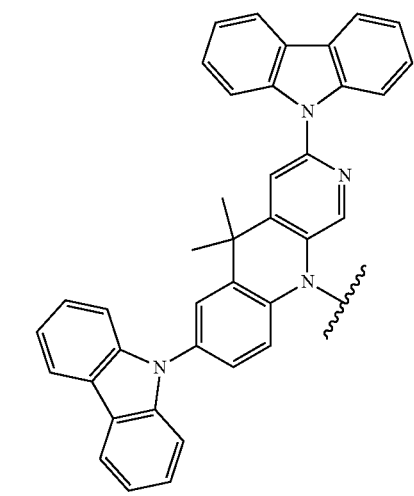

-continued
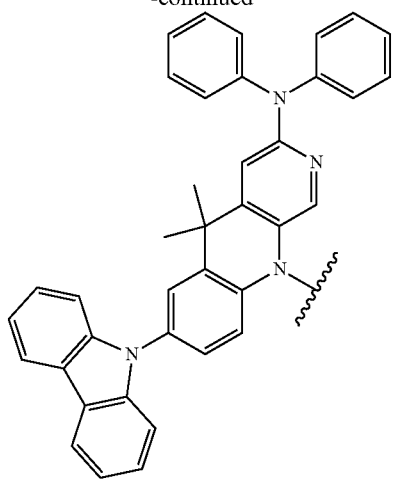
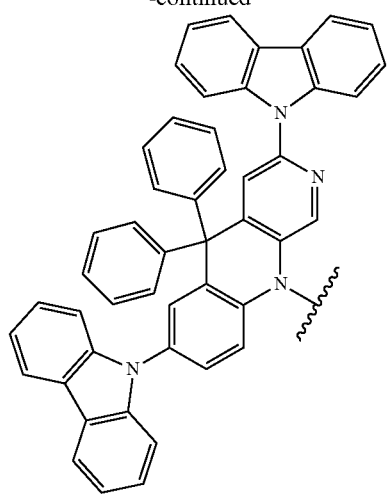
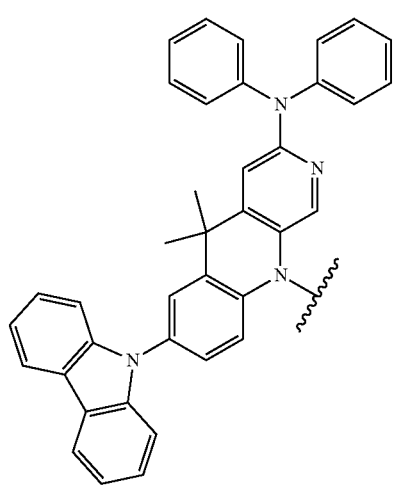
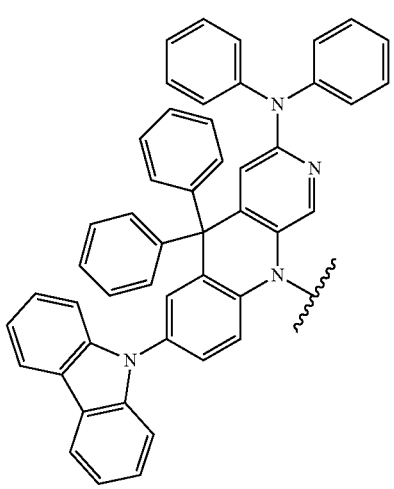
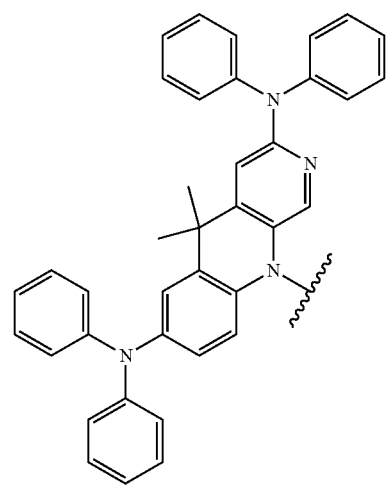
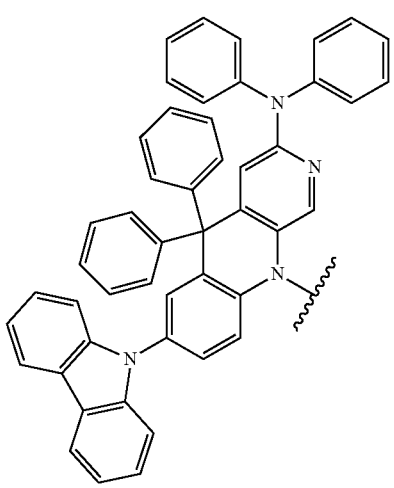

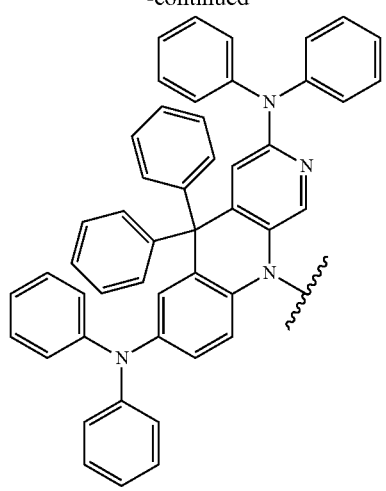
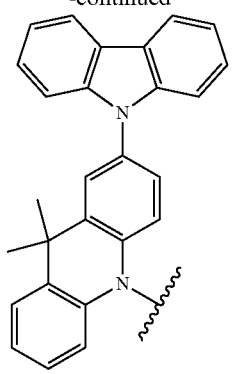
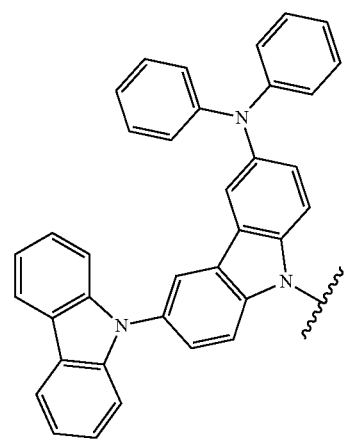
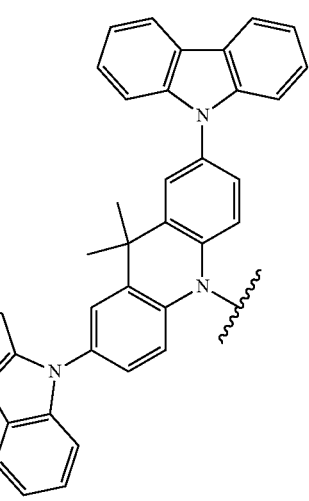
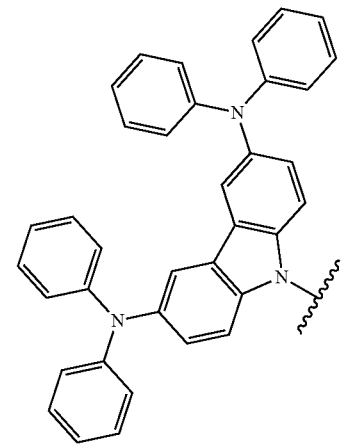
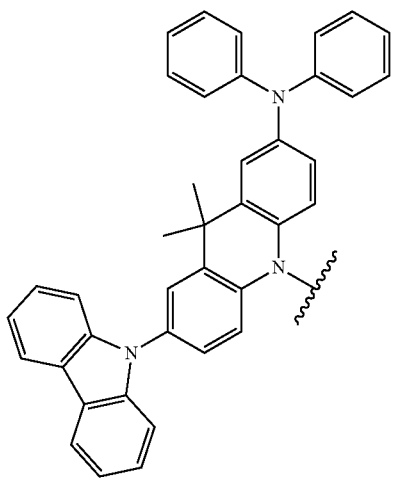
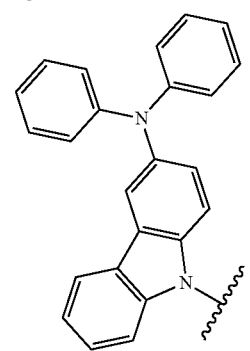
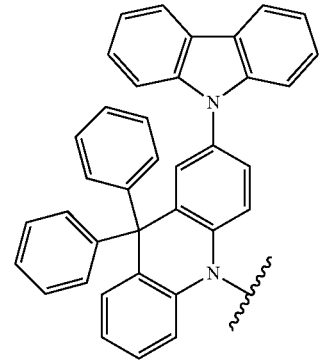

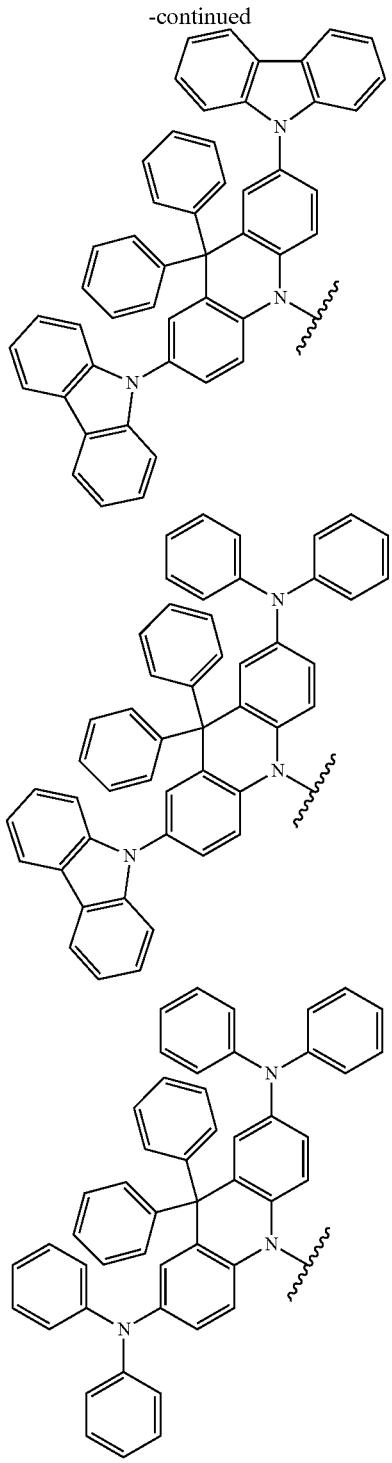

In Formula 1, Ar2 may be phenyl, and R may be methyl.

Since the organic compound of the present disclosure includes a chromenopyrazole core, the organic compound has high energy level of triplet state is increased. (high energy level of the triplet state)

In addition, in the organic compound of the present disclosure, since the chromenopyrazole core serve as an electron acceptor and an electron donor moiety, e.g., carbazole, is connected (or bonded) to the electron acceptor moiety, the organic compound of the present disclosure has a bipolar property (characteristic).

Accordingly, the organic light emitting diode and the OLED device including the organic compound as a host in the EML have advantages in the emitting efficiency and the lifespan.

For example, since the DPEPO compound, which has relatively high energy level of the triplet state and may be used as the host, has the n-type property, the recombination zone of the hole and the electron is not located in a center of the EML. However, since the organic compound of the present disclosure good balance of the hole and the electron due to the bipolar property with high energy level of the triplet state, the recombination zone of the hole and the electron is located in a center of the EML. Accordingly, the organic light emitting diode and the OLED device has improved emitting efficiency without lifespan decrease.

The organic compound of the present disclosure is included in the organic emitting layer 162, preferably the EML 240. The organic compound serves as a host, and the EML 240 may further includes a dopant. For example, the dopant may have a percentage by weight of about 1 to 40 with respect to the host. The dopant may be at least one of a delayed fluorescent dopant, a phosphorescent dopant and a fluorescent dopant.

When the EML 240 includes the delayed fluorescent dopant (delayed fluorescent compound) with the organic compound of the present disclosure as the host, a difference between the HOMO of the host "$HOMO_{Host}$" and the HOMO of the delayed fluorescent dopant "$HOMO_{Dopant}$" or a difference between the LUMO of the host "$LUMO_{Host}$" and the LUMO of the delayed fluorescent dopant "$LUMO_{Dopant}$" is less than about 0.5 eV. In this instance, the charge transfer efficiency from the host to the dopant may be improved.

The energy level of triplet state of the delayed fluorescent dopant is smaller than the energy level of triplet state of the host, and a difference between the energy level of singlet state of the delayed fluorescent dopant and the energy level of triplet state of the delayed fluorescent dopant is less than 0.3 eV. ($\Delta E_{ST} \leq 0.3$ eV.) As the difference "$\Delta E_{ST}$" is smaller, the emitting efficiency is higher. In addition, even if the difference "$\Delta E_{ST}$" between the energy level of singlet state of the delayed fluorescent dopant and the energy level of triplet state of the delayed fluorescent dopant is about 0.3 eV, which is relatively large, the excitons in the singlet state and the excitons in the triplet state can be transited into the intermediate state.

The EML 240 may include the organic compound of the present disclosure as the host with the delayed fluorescent dopant as a first dopant and the fluorescent dopant as a second dopant. The summation of the first dopant and the second dopant may be a percentage by weight of about 1 to 40 with respect to the host.

The energy level of singlet state of the first dopant may be smaller than that of the host and larger than that of the second dopant. The energy level of triplet state of the first dopant may be smaller than that of the host and larger than that of the second dopant.

Since the EML 240 includes the host and the first and second dopant, the emitting efficiency may be improved by the first dopant and the color purity may be improved by the second dopant. Namely, after the energy is transferred from the host into the first dopant, the singlet state energy and the triplet state energy of the first dopant is transferred into the second dopant, and the light emission is provided from the second dopant. As a result, the quantum efficiency (emitting efficiency) of the organic light emitting diode D is increased, and the full width at a half maximum (FWHM) of the organic light emitting diode D is narrowed.

The delayed fluorescent dopant as the first dopant has high quantum efficiency. However, since the light emitted from the delayed fluorescent dopant has wide FWHM, the light from the delayed fluorescent dopant has bad color purity. On the other hand, the fluorescent dopant as the second dopant has narrow FWHM and high color purity. However, since the triplet state energy of the fluorescent dopant is not involved in the light emission, the fluorescent dopant has low quantum efficiency.

However, since the EML 240 includes the first dopant, i.e., the delayed fluorescent compound, and the second dopant, i.e., the fluorescent dopant, the organic light emitting diode D has advantages in both the emitting efficiency and the color purity.

In addition, since the organic compound of the present disclosure, which has high energy level of triplet state and the bipolar property, is used as the host, the emitting efficiency of the organic light emitting diode D is further improved.

For example, the organic compound of the present disclosure in Formula 1 may be one of compounds in Formula 4.

[Formula 4]

Compound 1

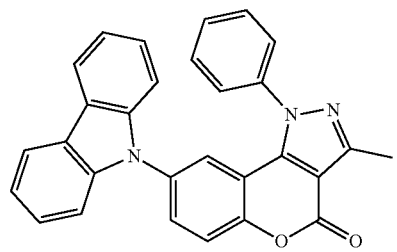

Compound 2

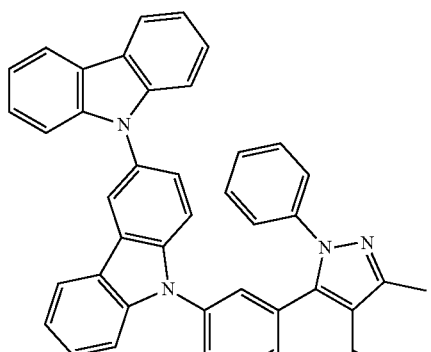

Compound 3

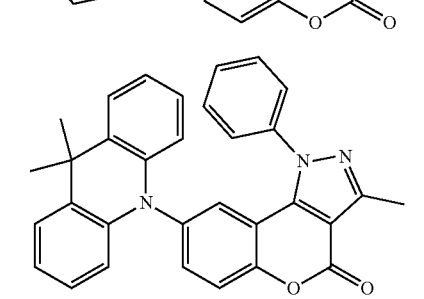

Compound 4

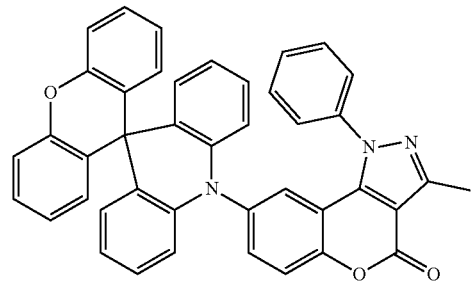

Compound 5

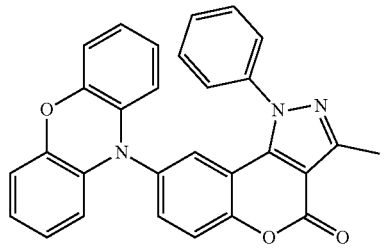

Compound 6

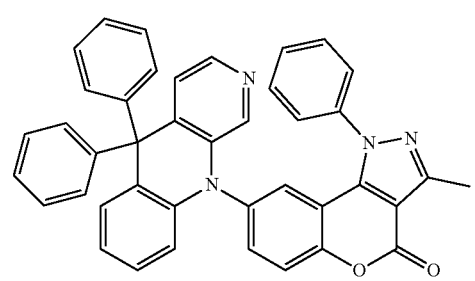

Compound 7

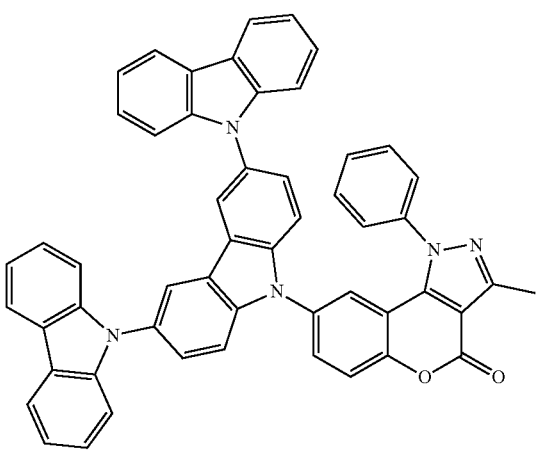

Compound 8
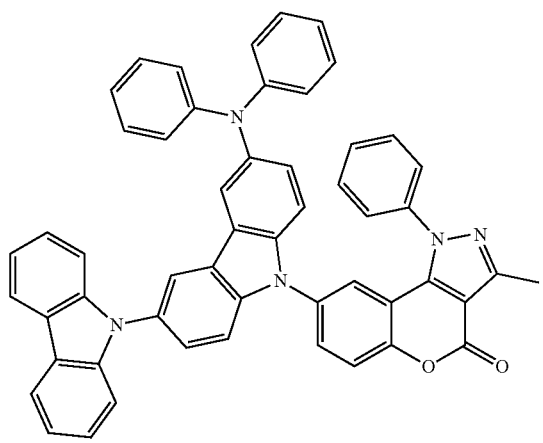
Compound 9
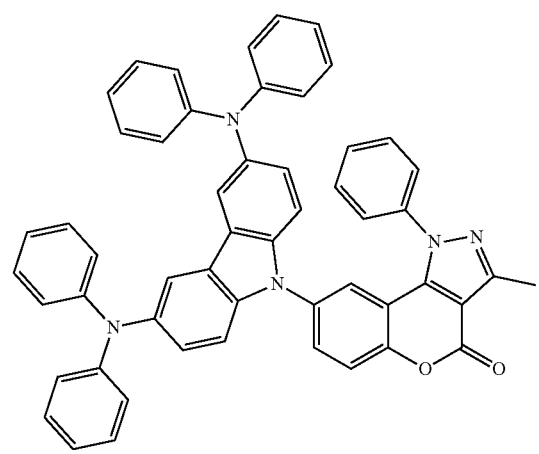
Compound 10
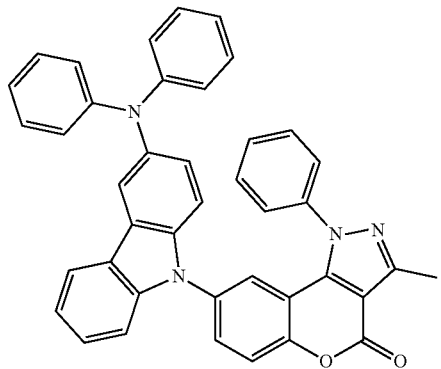
Compound 11
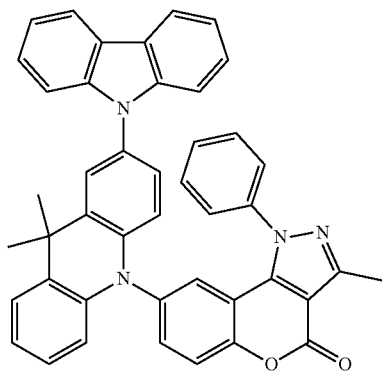
Compound 12
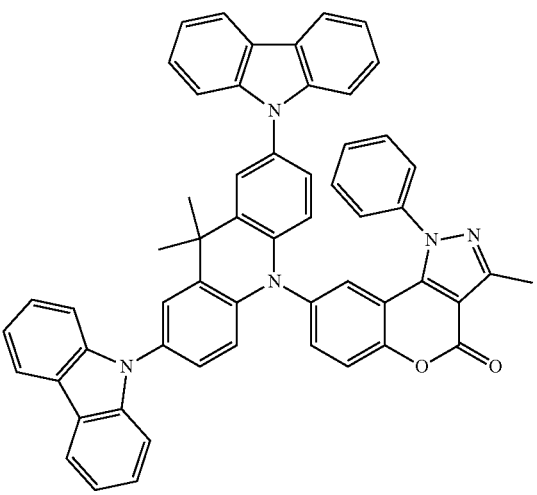
Compound 13
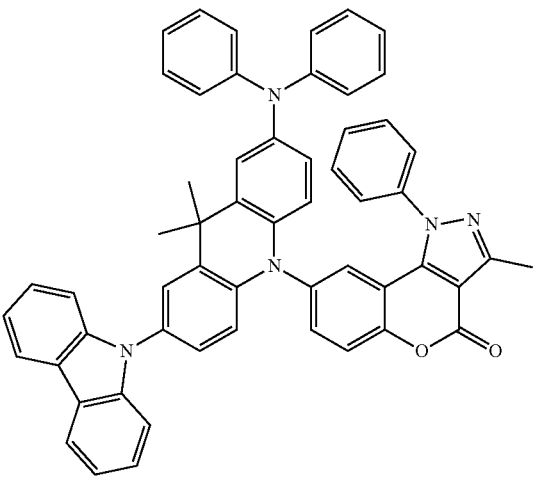

Compound 14
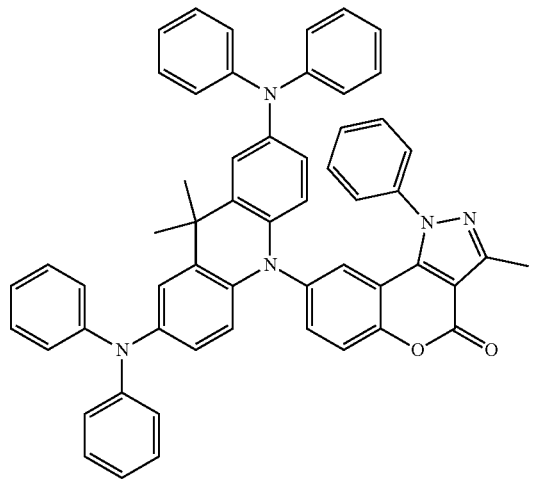
Compound 15
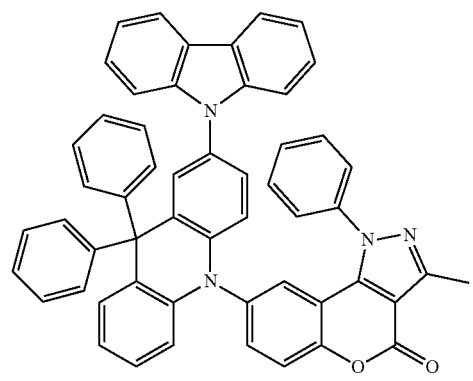
Compound 16
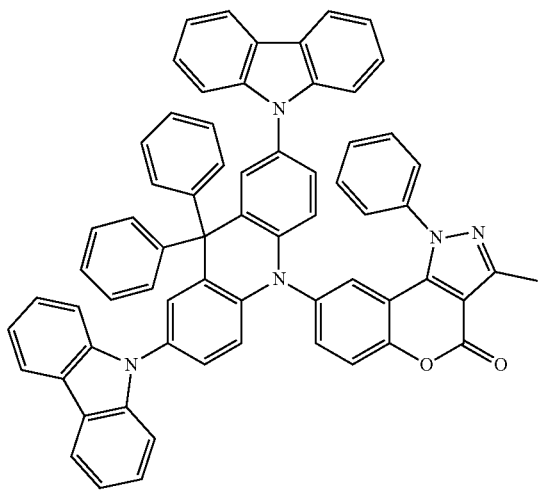
Compound 17
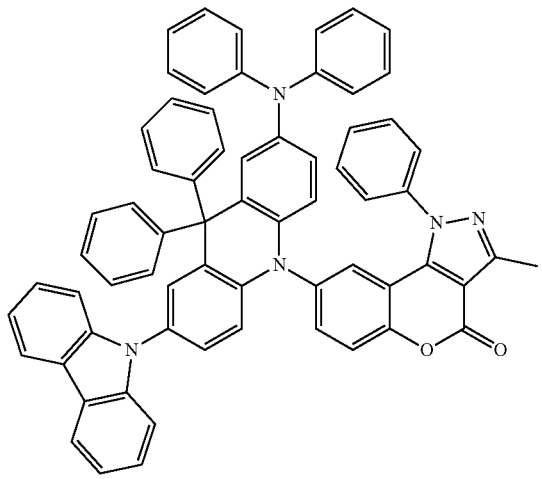
Compound 18
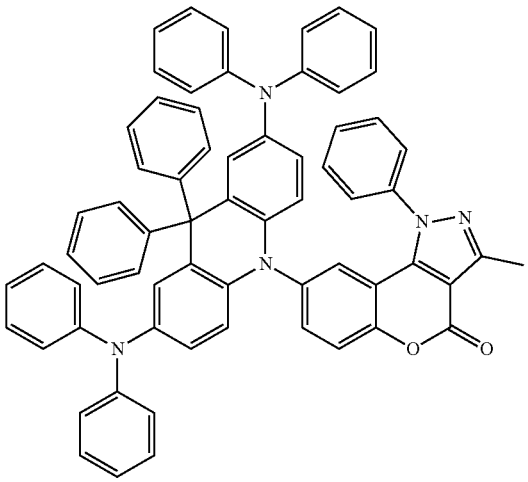
Compound 19
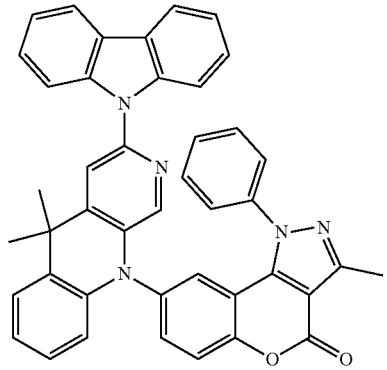

Compound 20
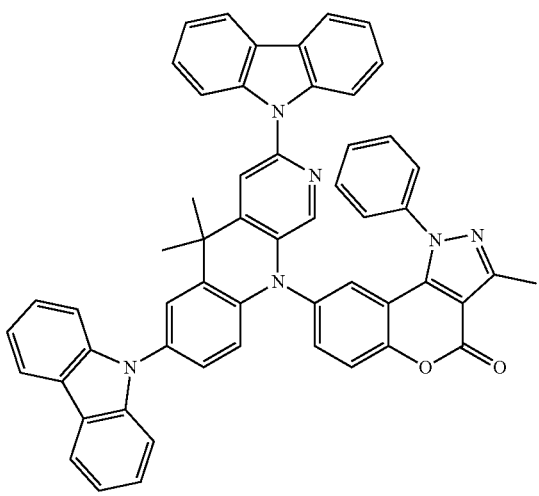
Compound 21
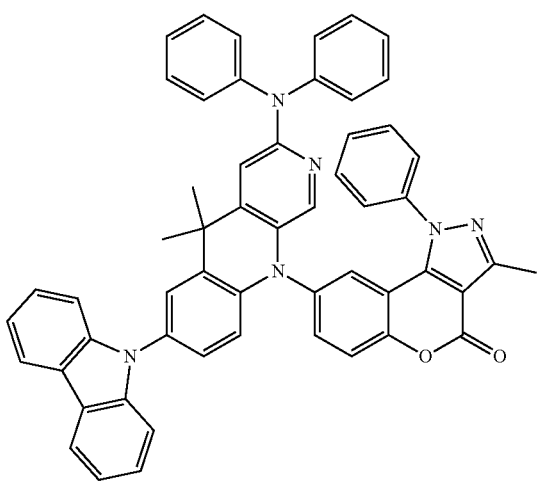
Compound 22
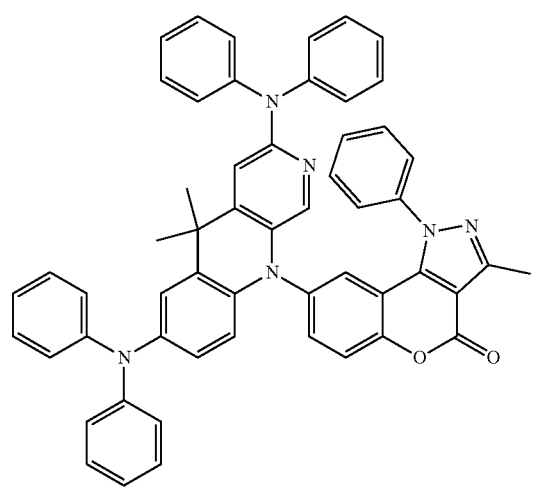
Compound 23
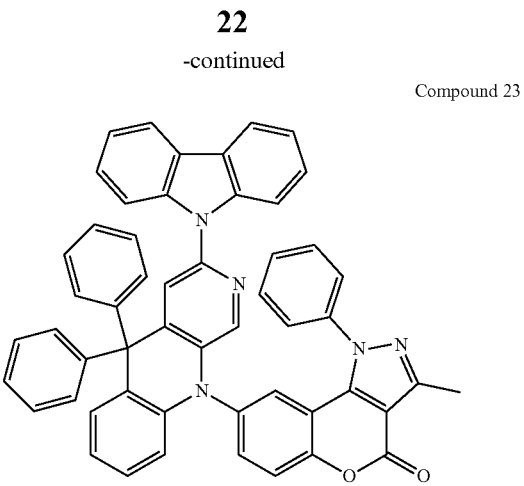
Compound 24
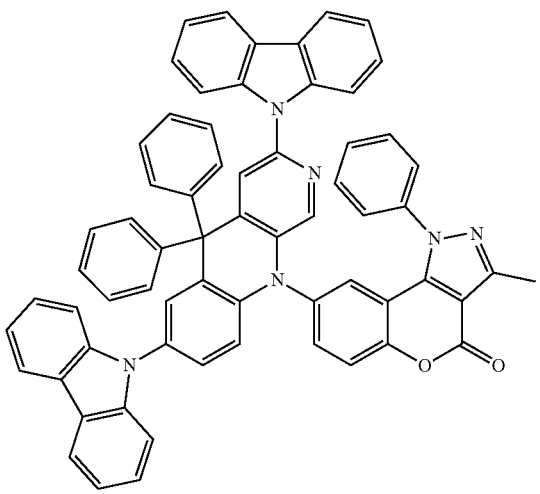
Compound 25
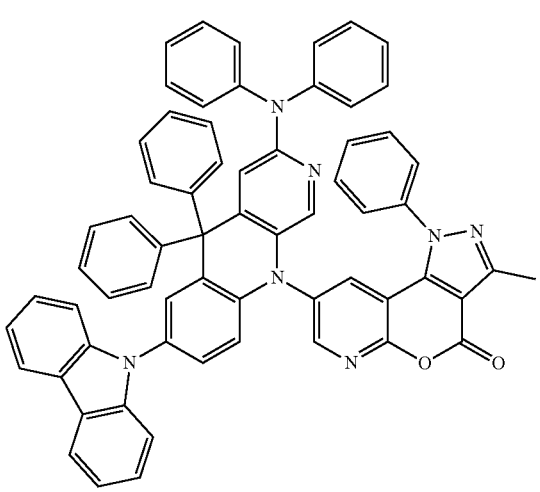

Compound 26

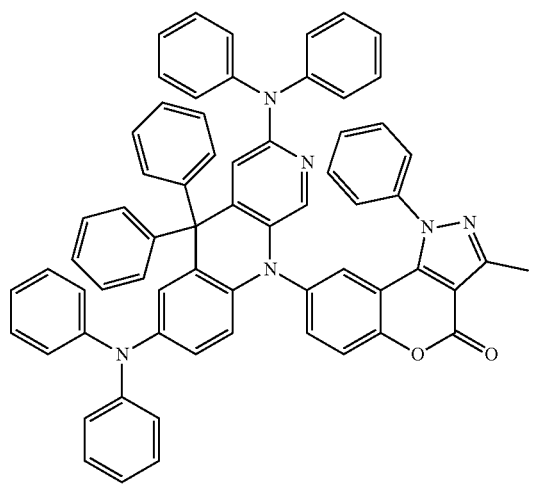

[Synthesis of Organic Compounds]

1. Synthesis of Compound 1

(1) Compound B

[Reaction Formula 1-1]

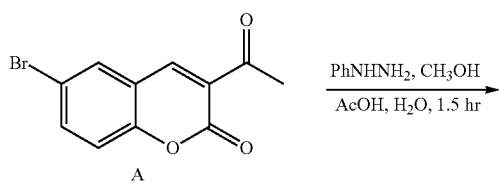

In the reaction vessel, Compound A (1.0 g, 3.8 mmol) was dissolved in methanol (5 ml) and stirred under the temperature of 60° C. After a mixed solution of phenylhydrazine (0.41 ml, 4.1 mmol), acetic acid (10 ml) and distilled water (5 ml) was slowly added into the reaction vessel using the dropping funnel, and the mixture was stirred for 30 minutes. The mixture was cooled into the room temperature, and the precipitate of orange-red color was separated by the reduced-pressure distillation. The precipitate was washed by distilled water such that Compound B was obtained. (1.26 g, yield=94%)

(2) Compound C

[Reaction Formula 1-2]

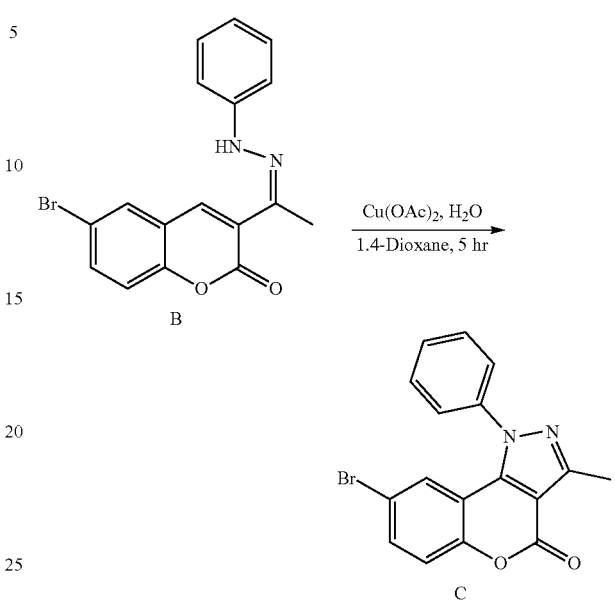

Copper(II) acetate monohydrate (0.34 g, 1.7 mmol) and Compound B (1.2 g, 3.4 mmol) were dissolved in 1,4-dioxane (100 ml) and stirred under the temperature of 70° C. for 5 hrs. The mixture was cooled to room temperature, and the precipitate was removed by the reduced-pressure distillation. Compound C was obtained by the silica-column chromatography using a mixed solution of ethyl acetate and hexane (volume ratio=1:9). (1.1 g, yield=92%)

(3) Compound 1

[Reaction Formula 1-3]

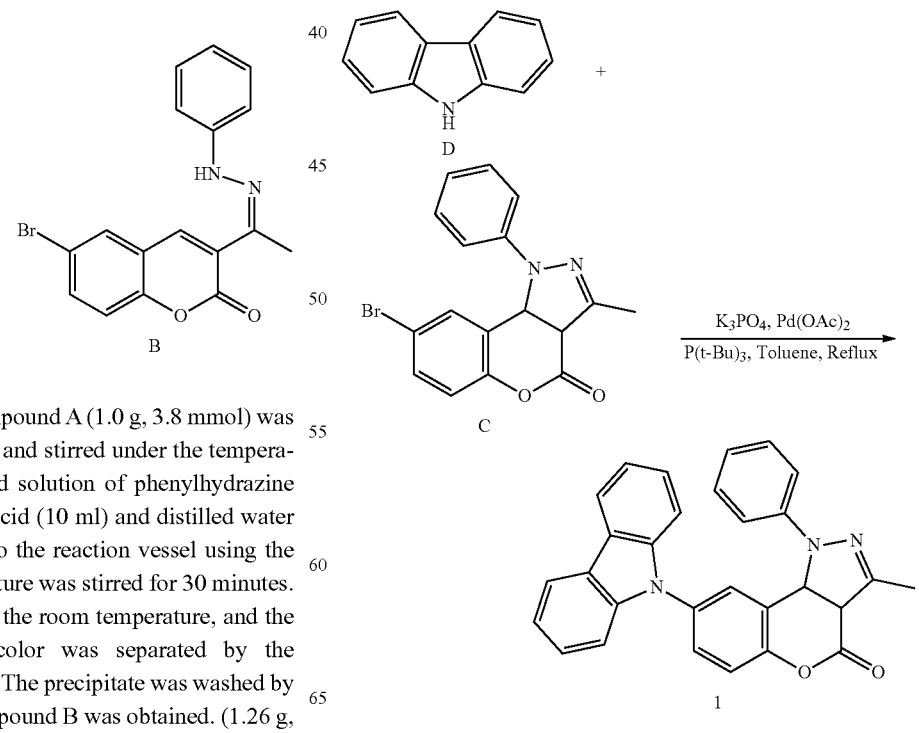

Under a nitrogen atmosphere, Compound C (1.0 g, 2.8 mmol), Compound D (0.52 g, 3.1 mmol) and K₃PO₄ (1.8 g, 8.4 mmol) were dissolved in toluene (30 ml) and refluxed for 15 minutes. The mixture was heated by the temperature of 60° C. Pd(OAc)₂ (0.019 g, 0.08 mmol) and tri-tert-butylphosphine (0.68 mL, 0.17 mmol, 50 wt % in xylene) were added into the mixture and refluxed for 8 hrs. After the mixture was cooled to room temperature and filtered by the decompression filter, the mixture was washed by CH₂Cl₂. After the crude was obtained by removing the organic layer, silica-gel chromatography using a mixed solution of CH₂Cl₂ and hexane (volume ratio=1:1) was performed such that Compound 1 in a white color was obtained. (1.15 g, yield=93%)

2. Synthesis of Compound 2

[Reaction Formula 2]

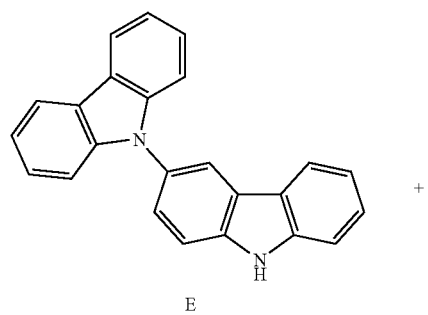

E

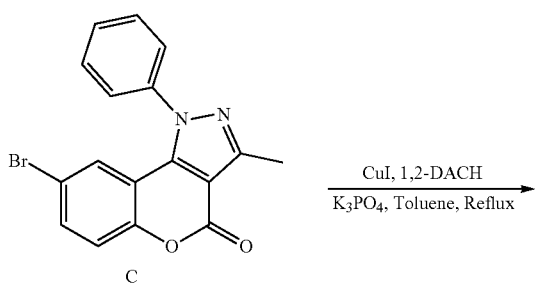

C

CuI, 1,2-DACH
K₃PO₄, Toluene, Reflux

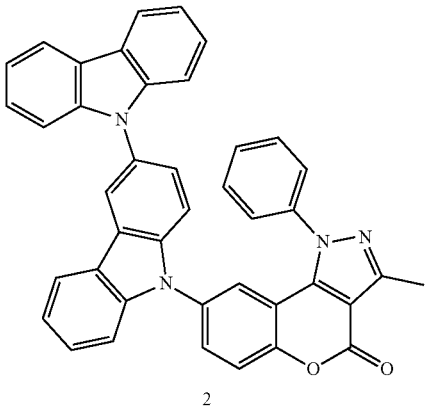

2

Compound E is used instead of Compound D in the synthesis of Compound 1 to obtain Compound 2. (2.2 g, yield=86%)

3. Synthesis of Compound 3

[Reaction Formula 3]

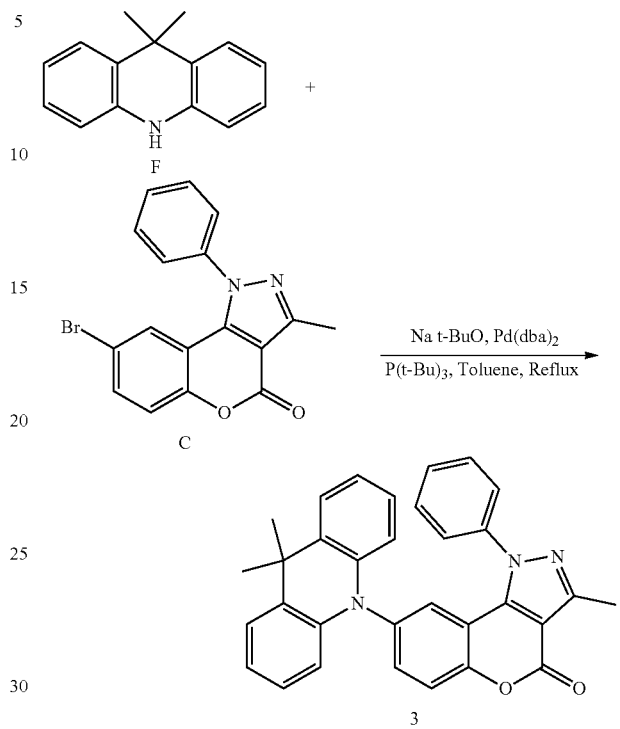

3

In the reaction vessel under a nitrogen atmosphere, Compound C (1.30 g, 3.66 mmol), Compound F (0.95 g, 4.54 mmol) and sodium tert-butoxide (1.00 g, 10.4 mmol) were dissolved in toluene (200 ml). A toluene solution (30 ml) including Pd(dba)₂ (0.3 g, 5.22 mmol) and P(tBu)₃ (0.22 g, 1.09 mmol) was slowly added into the reaction vessel and refluxed for 15 hrs. After the mixture was cooled to room temperature, the precipitate was removed using celite, and the solvent was dried. Compound 3 was obtained by silica-column chromatography. (1.52 g, yield=86%)

4. Synthesis of Compound 4

[Reaction Formula 4]

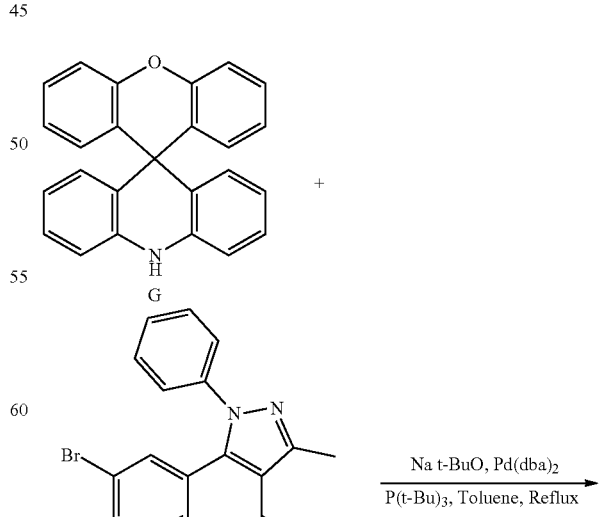

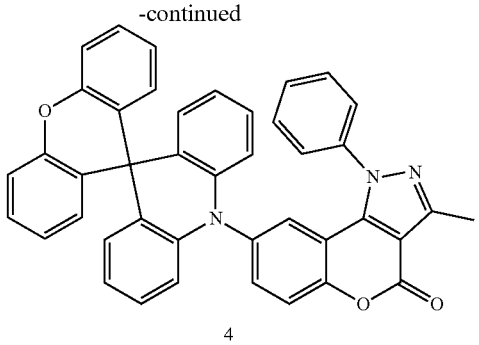

4

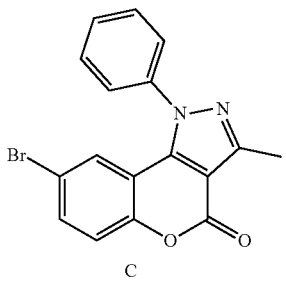

C

Compound G is used instead of Compound F in the synthesis of Compound 3 to obtain Compound 4. (1.68 g, yield=74%)

5. Synthesis of Compound 5
[Reaction Formula 5]

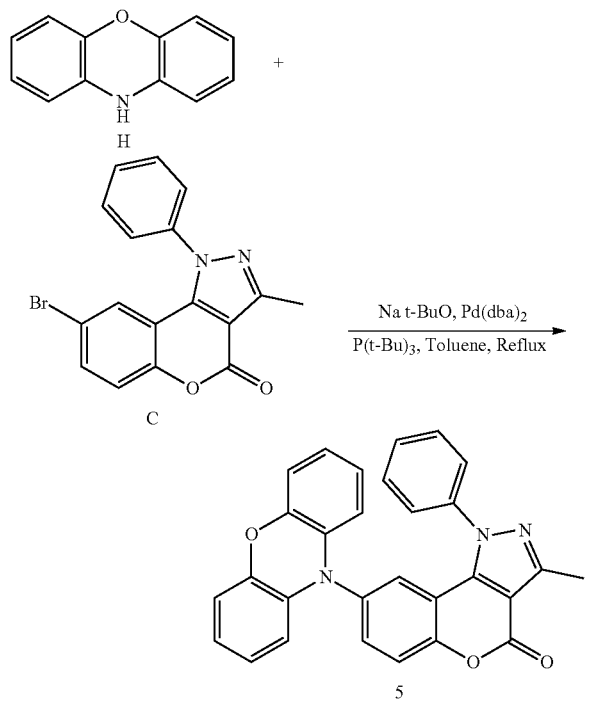

Compound H is used instead of Compound F in the synthesis of Compound 3 to obtain Compound 5. (1.26 g, yield=75%)

6. Synthesis of Compound 6
[Reaction Formula 6]

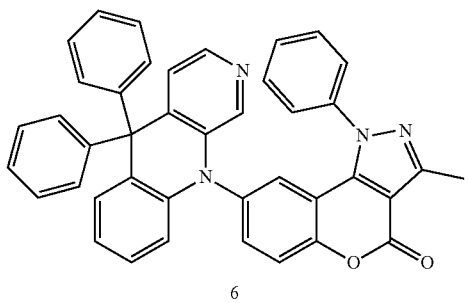

6

Compound I is used instead of Compound F in the synthesis of Compound 3 to obtain Compound 6. (1.09 g, yield=49%)

Figure 4A:
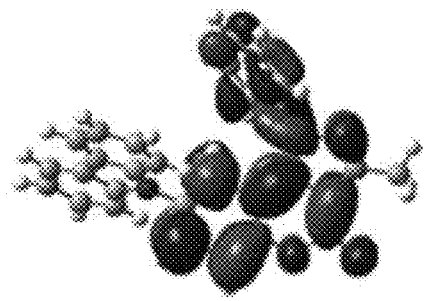
FIGS. 4A and 4B are views showing an LUMO distribution and a HOMO distribution of Compound 1 of the present disclosure, respectively.
Figure 4B:
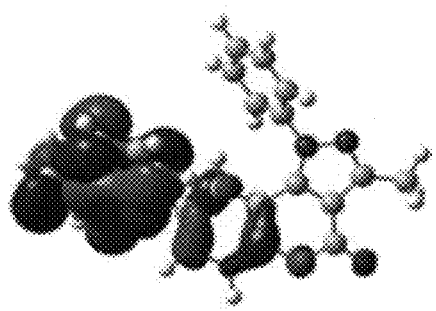
Figure 5A:
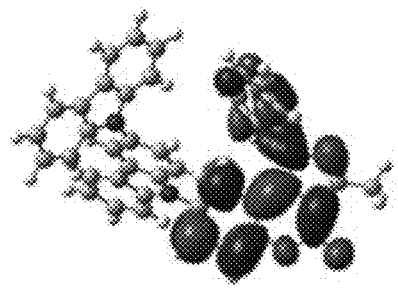
FIGS. 5A and 5B are views showing an LUMO distribution and a HOMO distribution of Compound 2 of the present disclosure, respectively.
Figure 5B:
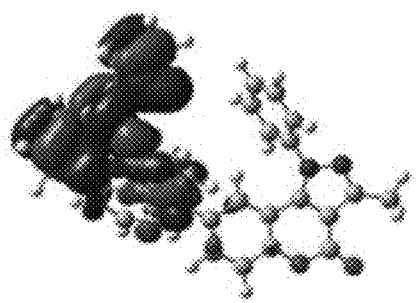
Figure 6A:
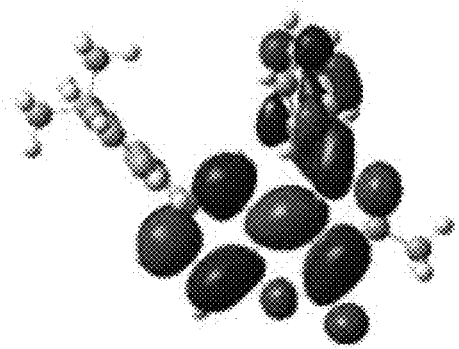
FIGS. 6A and 6B are views showing an LUMO distribution and a HOMO distribution of Compound 3 of the present disclosure, respectively.
Figure 6B:
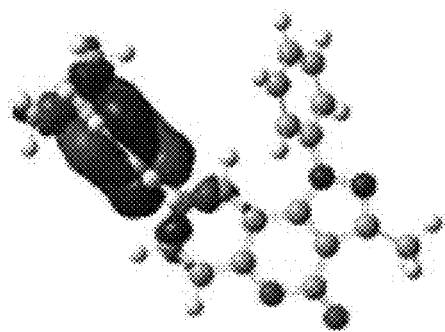
Figure 7A:
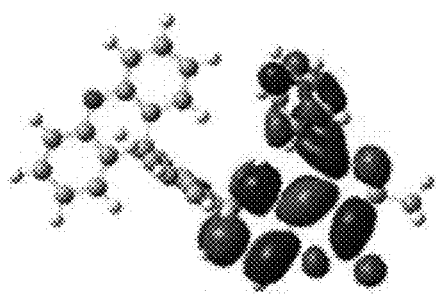
FIGS. 7A and 7B are views showing an LUMO distribution and a HOMO distribution of Compound 4 of the present disclosure, respectively.
Figure 7B:
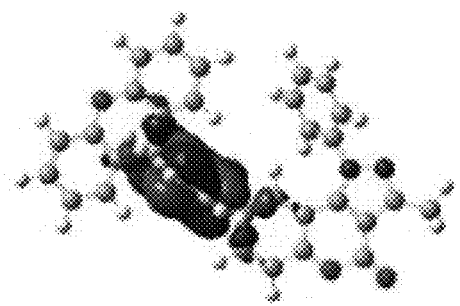
Figure 8A:
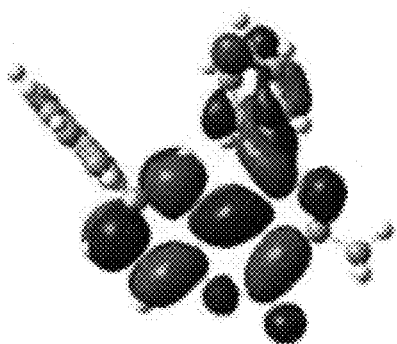
FIGS. 8A and 8B are views showing an LUMO distribution and a HOMO distribution of Compound 5 of the present disclosure, respectively.
Figure 8B:
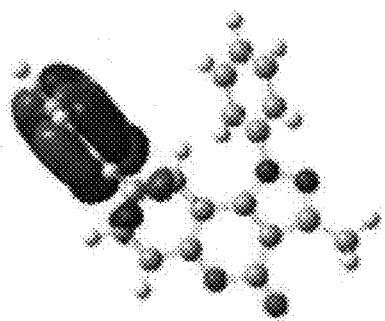
Figure 9A:
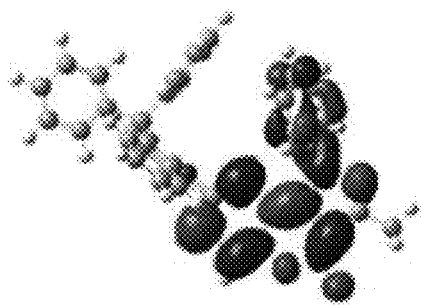
FIGS. 9A and 9B are views showing an LUMO distribution and a HOMO distribution of Compound 6 of the present disclosure, respectively.
Figure 9B:
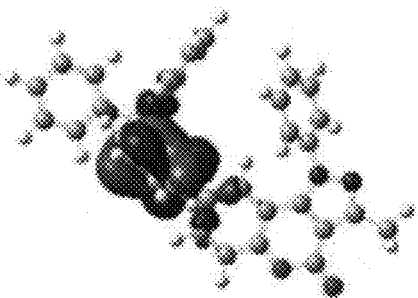

The physical properties, i.e., an energy level of HOMO, an energy level of LUMO, an energy band gap (Eg), an energy level of singlet state (S1) and an energy level of triplet state (T1), of Compounds 1 to 6 in Formula 4 was measured and these properties are listed in Table 1. (unit: [eV]). A LUMO distribution and a HOMO distribution of Compound 1 are respectively shown in FIGS. 4A and 4B, and an LUMO distribution and a HOMO distribution of Compound 2 are respectively shown in FIGS. 5A and 5B. A LUMO distribution and a HOMO distribution of Compound 3 are respectively shown in FIGS. 6A and 4B, and a LUMO distribution and a HOMO distribution of Compound 4 are respectively shown in FIGS. 7A and 7B. A LUMO distribution and a HOMO distribution of Compound 5 are respectively shown in FIGS. 8A and 8B, and a LUMO distribution and a HOMO distribution of the compound 6 are respectively shown in FIGS. 9A and 9B.

TABLE 1

|  | HOMO | LUMO | Eg | S1 | T1 |
| --- | --- | --- | --- | --- | --- |
| Compound 1 | −1.70 | −5.51 | 3.81 | 3.26 | 3.00 |
| Compound 2 | −1.80 | −5.25 | 3.45 | 3.08 | 2.97 |
| Compound 3 | −1.69 | −5.16 | 3.37 | 2.88 | 2.85 |
| Compound 4 | −1.76 | −5.20 | 3.44 | 2.86 | 2.82 |
| Compound 5 | −1.75 | −5.21 | 3.06 | 2.50 | 2.86 |
| Compound 6 | −1.67 | −5.25 | 3.58 | 3.00 | 2.97 |

As shown in Table 1, the organic compound of the present disclosure has a higher energy level of triplet state. Accordingly, the organic compound used as the host in the EML provides high energy efficiency.

[Hole Only Device]

In the vacuum chamber of about $10^{-7}$ Torr, layers are sequentially deposited on an ITO substrate.

(1) first HTL (20 nm, Formula 5), (2) host layer (50 nm), (3) second HTL (20 nm, Formula 5) and (4) cathode (100 nm, Al).

1. Example 1

The host layer is formed using Compound 3 of Formula 4.

2. Example 2

The host layer is formed using Compound 4 of Formula 4.

3. Comparative Example 1

The host layer is formed using the DPEPO compound.

[Formula 5]

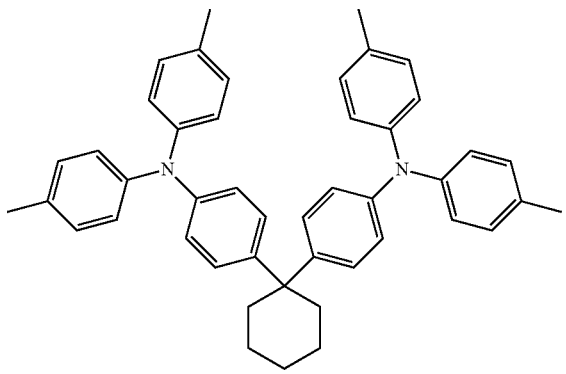

Figure 10:
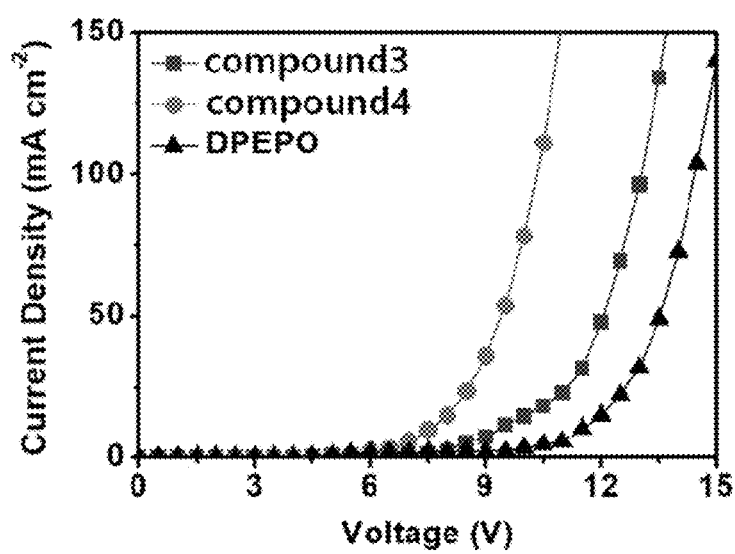
FIG. 10 is a graph showing a hole mobility property of the organic compound of the present disclosure.

The current density of the hole only device in Examples 1 and 2 and Comparative Example 1 was measured and shown in FIG. 10.

As shown in FIG. 10, in comparison to the hole only device using the DPEPO compound as the host, a hole mobility of the hole only device using the organic compound of the present disclosure is improved.

[Electron Only Device]

In the vacuum chamber of about $10^{-7}$ Torr, layers are sequentially deposited on an ITO substrate.

(1) first ETL (20 nm, Formula 6), (2) host layer (50 nm), (3) second ETL (20 nm, Formula 6), (4) EIL (1.5 nm, LiF), and (5) cathode (100 nm, Al).

1. Example 3

The host layer is formed using Compound 3 of Formula 4.

2. Example 4

The host layer is formed using Compound 4 of Formula 4.

3. Comparative Example 2

The host layer is formed using the DPEPO compound.

[Formula 6]

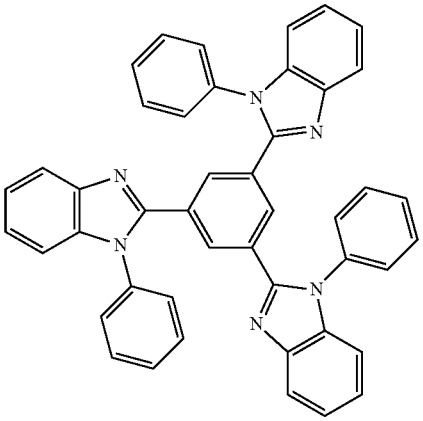

Figure 11:
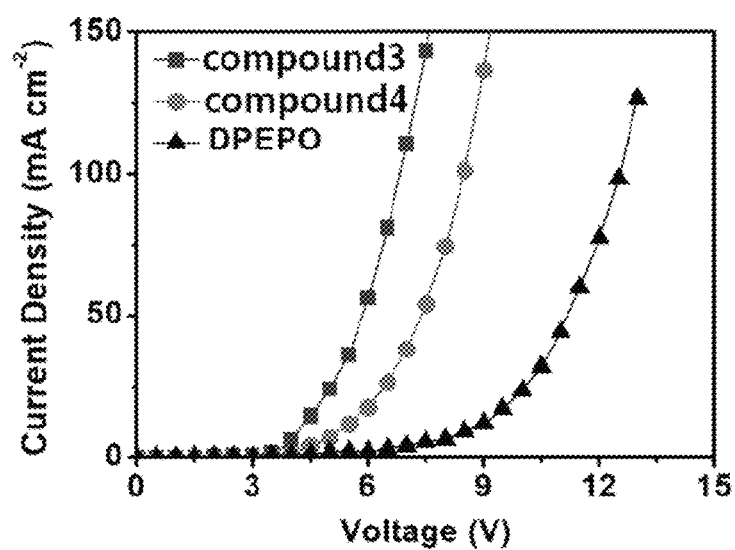
FIG. 11 is a graph showing an electron mobility property of the organic compound of the present disclosure.

The current density of the electron only device in Examples 3 and 4 and Comparative Example 2 is measured and shown in FIG. 11.

As shown in FIG. 11, in comparison to the electron only device using the DPEPO compound as the host, an electron mobility of the electron only device using the organic compound of the present disclosure is improved.

[Organic Light Emitting Diode]

In the vacuum chamber of about $10^{-7}$ Torr, layers are sequentially deposited on an ITO substrate. The dopant of a delayed fluorescent compound is used.

(a) HIL (70 Å, Formula 7), (b) HTL (500 Å, Formula 5), (c) EBL (100 Å, Formula 8), (d) EML (250 Å, Host: Dopant (10 wt %, Formula 9)), (e) HBL (50 Å, Formula 10), (f) ETL (250 Å, Formula 6), (g) EIL (15 Å, LiF), and (h) Cathode (1000 Å, Al).

[Formula 7]

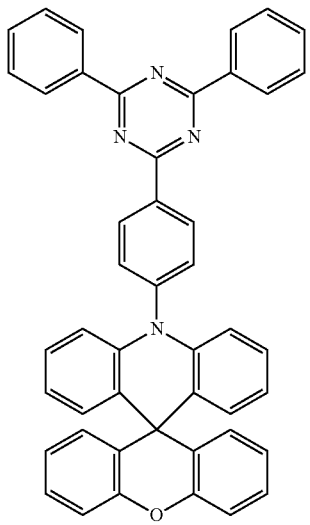

(1) Example 5 (Ex5)

Compound 1 of Formula 4 was used as the host.

(2) Example 6 (Ex6)

Compound 2 of Formula 4 was used as the host.

(3) Example 7 (Ex7)

Compound 3 of Formula 4 was used as the host.

(4) Example 8 (Ex8)

Compound 4 of Formula 4 was used as the host.

(5) Example 9 (Ex9)

Compound 5 of Formula 4 was used as the host.

(6) Example 10 (Ex10)

Compound 6 of Formula 4 was used as the host.

[Formula 7]

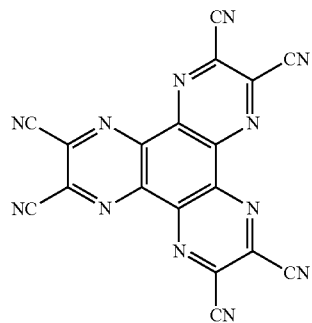

[Formula 8]

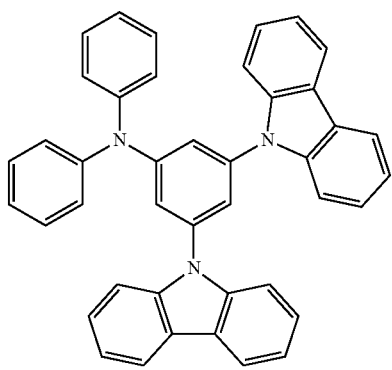

[Formula 9]

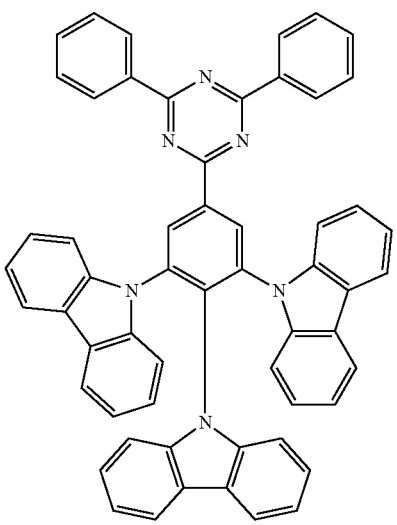

[Formula 10]

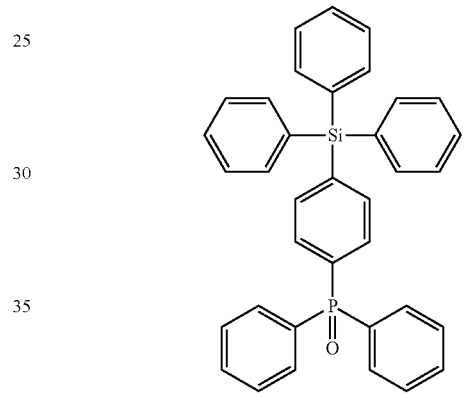

The properties of the organic light emitting diodes of and Ex5 to Ex10 were measured. The driving voltage ($V_{on}$), the emission peak ($\lambda_{max}$), the current efficiency (CE), the power efficiency (PE), the external quantum efficiency (EQE) and the CIE color coordinate of the organic light emitting diodes were measured using the current supply source "KEITHLEY" and the photometer "PR 650" and listed in Table 2.

TABLE 2

| | $V_{on}$ (V)[a] | $\lambda_{max}$ (nm)[b] | CE (cd A$^{-1}$)[c] | PE (lm W$^{-1}$)[e] | EQE (%)[f] | CIE (x, y)[g] |
|---|---|---|---|---|---|---|
| Ex 5 | 3.3 | 470 | 40.5 | 36.3 | 27.9, 23.3, 14.5 | 0.15, 0.21 |
| Ex 6 | 3.3 | 478 | 27.0 | 28.0 | 17.0, 16.5, 15.1 | 0.17, 0.27 |
| Ex 7 | 3.5 | 478 | 20.4 | 18.2 | 12.6, 10.4, 9.8 | 0.16, 0.28 |
| Ex 8 | 3.5 | 480 | 23.1 | 19.8 | 14.2, 11.6, 7.6 | 0.17, 0.30 |
| Ex 9 | 3.5 | 476 | 25.6 | 21.0 | 15.1, 14.0, 11.3 | 0.16, 0.26 |
| Ex 10 | 3.5 | 476 | 24.0 | 20.8 | 14.8, 12.6, 10.2 | 0.16, 0.26 |

[a] Turn-on voltage at a brightness of 1 cd m$^{-2}$.
[b] Maximum EL wavelength at 1000 cd m$^{-2}$.
[c] Maximum current efficiency.
[e] Maximum power efficiency.
[f] External quantum efficiency at maximum value, 100 and 500 cd m$^{-2}$.
[g] Commission Inernationale de l'Elcairage at 1000 cd m$^{-2}$.

As shown in Table 2, the organic light emitting didoes of Ex5 to Ex10 using the organic compounds of the present disclosure as the host provide high emitting efficiency.

Figure 12:
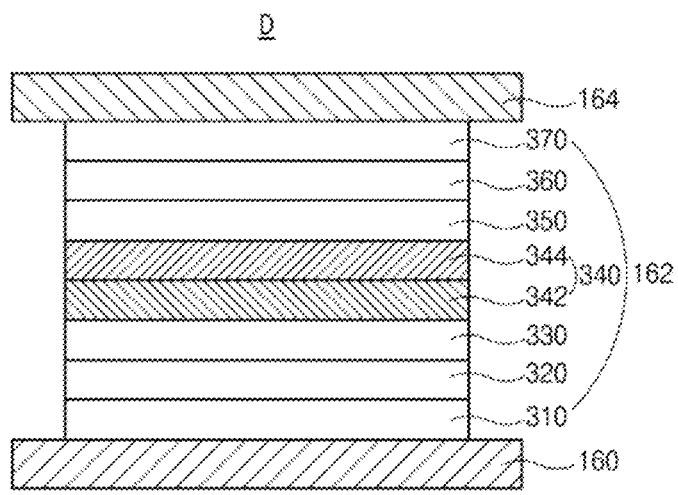
FIG. 12 is a schematic cross-sectional view of an organic light emitting diode according to a second embodiment of the present disclosure.

FIG. 12 is a schematic cross-sectional view of an organic light emitting diode according to a second embodiment of the present disclosure.

As shown in FIG. 12, an organic light emitting diode D includes the first and second electrodes 160 and 164, which face each other, and the organic emitting layer 162 therebetween. The organic emitting layer 162 includes an EML 340, which includes first and second layers 342 and 344 and is positioned between the first and second electrodes 160 and 164, a HTL 320 between the first electrode 160 and the EML 340 and an ETL 360 between the second electrode 164 and the EML 340.

In addition, the organic emitting layer 162 may further include a HIL 310 between the first electrode 160 and the HTL 320 and an EIL 370 between the second electrode 164 and the ETL 360.

Moreover, the organic emitting layer 162 may further include an EBL 330 between the HTL 320 and the EML 340 and a HBL 350 between the EML 340 and the ETL 360.

For example, in the EML 340, the first layer 342 (e.g., a first emitting material layer) may include the organic compound of the present disclosure as a first host and a delayed fluorescent dopant as a first dopant, and the second layer 344 (e.g., a second emitting material layer) may include a second host and a fluorescent dopant as a second dopant. Alternatively, the second layer 344 may include the organic compound of the present disclosure as a first host and a delayed fluorescent dopant as a first dopant, and the first layer 342 may include a second host and a fluorescent dopant as a second dopant. The second host may be the organic compound of the present disclosure. The delayed fluorescent dopant has an energy level of singlet state being larger than the fluorescent dopant.

The organic light emitting diode, where the first layer 342 includes the delayed fluorescent dopant and the second layer 344 includes the fluorescent dopant, will be explained.

In the organic light emitting diode D, an energy level of the singlet state and the energy level of the triplet state of the delayed fluorescent dopant are transferred into the fluorescent dopant such that the emission is generated from the fluorescent dopant. Accordingly, the quantum efficiency of the organic light emitting diode D is increased, and the FWHM of the organic light emitting diode D is narrowed.

The delayed fluorescent dopant as the first dopant has high quantum efficiency. However, since the light emitted from the delayed fluorescent dopant has wide FWHM, the light from the delayed fluorescent dopant has bad color purity. On the other hand, the fluorescent dopant as the second dopant has narrow FWHM and high color purity. However, since the energy level of the triplet state of the fluorescent dopant is not involved in the emission, the fluorescent dopant has low quantum efficiency.

Since the EML 340 of the organic light emitting diode D in the present disclosure includes the first layer 342, which includes the delayed fluorescent dopant, and the second layer 344, which includes the fluorescent dopant, the organic light emitting diode D has advantages in both the emitting efficiency and the color purity.

The energy level of the triplet state of the delayed fluorescent dopant is converted into the energy level of the singlet state of the delayed fluorescent dopant by the RISC effect, and the energy level of the singlet state of the delayed fluorescent dopant is transferred into the energy level of the singlet state of the fluorescent dopant. Namely, the difference between the energy level of the triplet state of the delayed fluorescent dopant and the energy level of the singlet state of the delayed fluorescent dopant is less than 0.3 eV such that the energy level of the triplet state of the delayed fluorescent dopant is converted into the energy level of the singlet state of the delayed fluorescent dopant by the RISC effect.

As a result, the delayed fluorescent dopant has an energy transfer function, and the first layer 342 including the delayed fluorescent dopant is not involved in the emission. The emission is generated in the second layer 344 including the fluorescent dopant.

The energy level of the triplet state of the delayed fluorescent dopant is converted into the energy level of the singlet state of the delayed fluorescent dopant by the RISC effect. In addition, since the energy level of the singlet state of the delayed fluorescent dopant is higher than that of the fluorescent dopant, the energy level of the singlet state of the delayed fluorescent dopant is transferred into the energy level of the singlet state of the fluorescent dopant. As a result, the fluorescent dopant emits the light using the energy level of the singlet state and the energy level of the triplet state such that the quantum efficiency (emitting efficiency) of the organic light emitting diode D is improved.

In other words, the organic light emitting diode D and the OLED device 100 (of FIG. 2) including the organic light emitting diode D has advantages in both the emitting efficiency and the color purity.

In each of the first and second layers 342 and 344, the first and second hosts may have a percentage by weight being larger than the delayed fluorescent dopant and the fluorescent dopant, respectively. In addition, the percentage by weight of the delayed fluorescent dopant in the first layer 342 may be greater than that of the fluorescent dopant in the second layer 344. As a result, the energy transfer from the delayed fluorescent dopant into the fluorescent dopant is sufficiently generated.

The energy level of the singlet state of the first host is greater than that of the delayed fluorescent dopant, and the energy level of the triplet state of the first host is greater than that of the delayed fluorescent dopant. In addition, the energy level of the singlet state of the second host is greater than that of the fluorescent dopant.

When not satisfying this condition, a quenching happens at the first and second dopants or an energy transfer from the host to the dopant does not happen, and thus the quantum efficiency of the organic light emitting diode D is reduced.

As mentioned above, since the organic compound of the present disclosure has high energy level of the triplet state, the energy transfer efficiency into the delayed fluorescent compound is increased such that the emitting efficiency of the organic light emitting diode D is improved. In addition, the reverse-transition of the excitons, which are generated from the delayed fluorescent dopant, into the host is sufficiently prevented.

Moreover, since the organic compound of the present disclosure having the bipolar property is included in the first layer 342 and/or the second layer 344 as the host, the recombination zone of the hole and the electron is located in a center of the first layer 342 and/or the second layer 344. Accordingly, the emitting efficiency and the lifespan of the organic light emitting diode D are improved.

For example, the second host, which is included in the second layer 344 with the fluorescent dopant, may be same as a material of the HBL 350. In this instance, the second layer 344 may have a hole blocking function with an emission function. Namely, the second layer 344 may serve as a buffer layer for blocking the hole. When the HBL 350 is omitted, the second layer 344 serves as an emitting layer and a hole blocking layer.

When the first layer 342 includes the fluorescent dopant and the second layer 344 includes the delayed fluorescent dopant, the first host of the first layer 342 may be same as a material of the EBL 330. In this instance, the first layer 342 may have an electron blocking function with an emission function. Namely, the first layer 342 may serve as a buffer layer for blocking the electron. When the EBL 330 is omitted, the first layer 342 serves as an emitting layer and an electron blocking layer.

Figure 13:
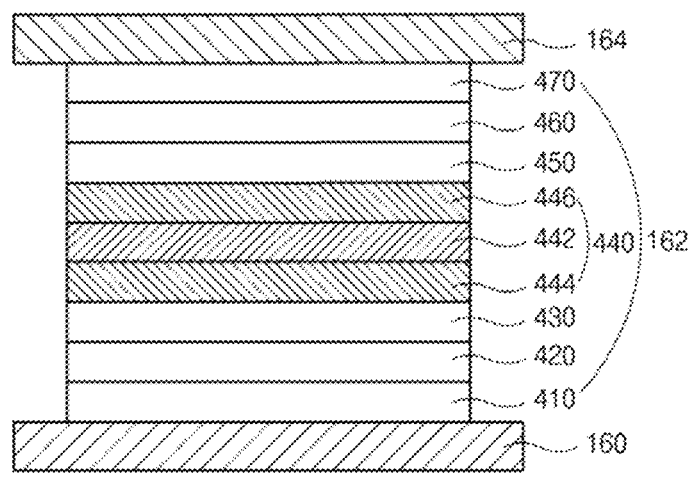
FIG. 13 is a schematic cross-sectional view of an organic light emitting diode according to a third embodiment of the present disclosure.

FIG. 13 is a schematic cross-sectional view of an organic light emitting diode of the present disclosure.

As shown in FIG. 13, an organic light emitting diode D includes the first and second electrodes 160 and 164, which face each other, and the organic emitting layer 162 therebetween. The organic emitting layer 162 includes an EML 440, which includes first to third layers 442, 444 and 446 and is positioned between the first and second electrodes 160 and 164, a HTL 420 between the first electrode 160 and the EML 440 and an ETL 460 between the second electrode 164 and the EML 440.

In addition, the organic emitting layer 162 may further include a HIL 410 between the first electrode 160 and the HTL 420 and an EIL 470 between the second electrode 164 and the ETL 460.

Moreover, the organic emitting layer 162 may further include an EBL 430 between the HTL 420 and the EML 440 and a HBL 450 between the EML 440 and the ETL 460.

In the EML 440, the first layer 442 is positioned between the second layer 444 and the third layer 446. Namely, the second layer 444 is positioned between the EBL 430 and the first layer 442, and the third layer 446 is positioned between the first layer 442 and the HBL 450.

The first layer 442 (e.g., a first emitting material layer) may include the organic compound of the present disclosure as a first host and a delayed fluorescent dopant as a first dopant, and the second layer 444 (e.g., a second emitting material layer) may include a second host and a fluorescent dopant as a second dopant. The third layer 446 (e.g., a third emitting material layer) may include a third host and a fluorescent dopant as a third dopant. The fluorescent dopant in the second and third layers 444 and 446 may be same or different. The second and third hosts may be the organic compound of the present disclosure. The delayed fluorescent dopant has an energy level of the singlet state being larger than the fluorescent dopant.

In the organic light emitting diode D, the energy level of the singlet state and the energy level of the triplet state of the delayed fluorescent dopant are transferred into the fluorescent dopant in the second layer 444 and/or the third layer 446 such that the emission is generated from the fluorescent dopant. Accordingly, the quantum efficiency of the organic light emitting diode D is increased, and the FWHM of the organic light emitting diode D is narrowed.

In each of the first to third layers 442, 444 and 446, the first to third hosts may have a percentage by weight being larger than the first to third dopants, respectively. In addition, the percentage by weight of the delayed fluorescent dopant (i.e., the first dopant) in the first layer 442 may be greater than that of each of the fluorescent dopant (i.e., the second dopant) in the second layer 444 and the fluorescent dopant (i.e., the third dopant) in the third layer 446.

The energy level of the singlet state of the first host is greater than that of the delayed fluorescent dopant, and the energy level of the triplet state of the first host is greater than that of the delayed fluorescent dopant. In addition, the energy level of the singlet state of the second host is greater than that of the fluorescent dopant in the second layer 444, and the energy level of the singlet state of the third host is greater than that of the fluorescent dopant in the third layer 446.

As mentioned above, since the organic compound of the present disclosure has high energy level of the triplet state, the energy transfer efficiency into the delayed fluorescent compound is increased such that the emitting efficiency of the organic light emitting diode D is improved. In addition, the reverse-transition of the excitons, which are generated from the delayed fluorescent dopant, into the host is sufficiently prevented.

Moreover, since the organic compound of the present disclosure having the bipolar property is included in the first layer 442 and/or each of the second and third layers 444 and 446 as the host, the recombination zone of the hole and the electron is located in a center of the first layer 442 and/or each of the second and third layers 444 and 446. Accordingly, the emitting efficiency and the lifespan of the organic light emitting diode D are improved.

For example, the second host in the second layer 444 may be same as a material of the EBL 430. In this instance, the second layer 444 may have an electron blocking function with an emission function. Namely, the second layer 444 may serve as a buffer layer for blocking the electron. When the EBL 430 is omitted, the second layer 444 serves as an emitting layer and an electron blocking layer.

The third host in the third layer 446 may be same as a material of the HBL 450. In this instance, the third layer 446 may have a hole blocking function with an emission function. Namely, the third layer 446 may serve as a buffer layer for blocking the hole. When the HBL 450 is omitted, the third layer 446 serves as an emitting layer and a hole blocking layer.

The second host in the second layer 444 may be same as a material of the EBL 430, and the third host in the third layer 446 may be same as a material of the HBL 450. In this instance, the second layer 444 may have an electron blocking function with an emission function, and the third layer 446 may have a hole blocking function with an emission function. Namely, the second layer 444 may serve as a buffer layer for blocking the electron, and the third layer 446 may serve as a buffer layer for blocking the hole. When the EBL 430 and the HBL 450 are omitted, the second layer 444 serves as an emitting layer and an electron blocking layer and the third layer 446 serves as an emitting layer and a hole blocking layer.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An organic compound having a structure of formula 1:

[Formula 1]

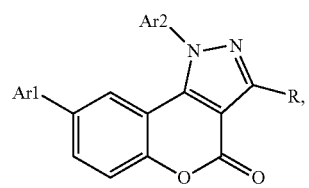

wherein Ar1 is a heteroaryl group comprising a nitrogen atom, and Ar2 is a $C_6$ to $C_{30}$ aryl group, and wherein R is a $C_1$ to $C_{10}$ alkyl group.

2. The organic compound according to claim 1, wherein Ar1 is selected from Formula 2:

[Formula 2]

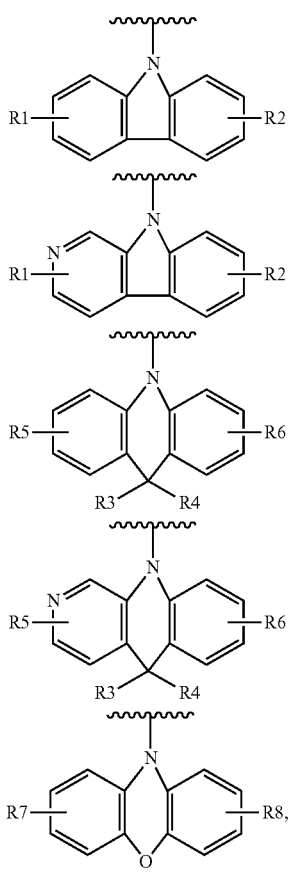

wherein each of R1, R2 and R5 to R8 is independently selected from the group consisting of hydrogen, carbazolyl and arylamine group, and wherein each of R3 and R4 is independently selected from the group consisting of $C_1$ to $C_{10}$ alkyl and $C_6$ to $C_{30}$ aryl, or R3 and R4 form a fused-ring.

3. The organic compound according to claim 1, wherein the organic compound is selected from the group consisting of:

Compound 1

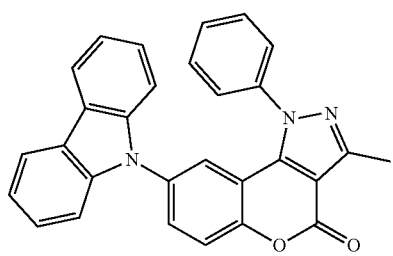

Compound 2

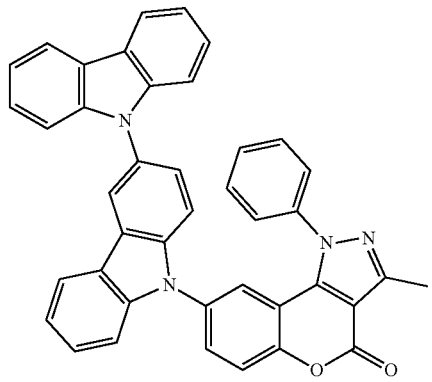

Compound 3

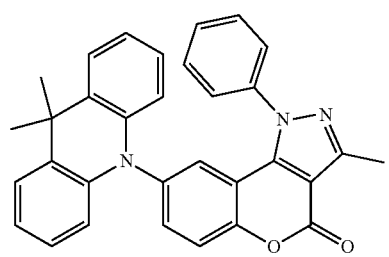

Compound 4

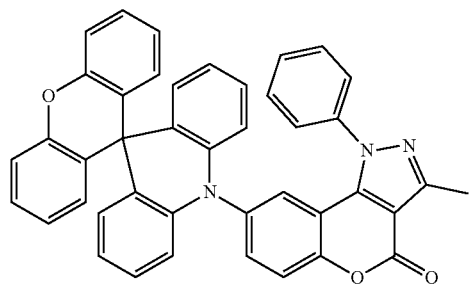

Compound 5

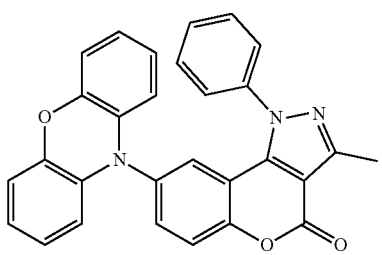

Compound 6

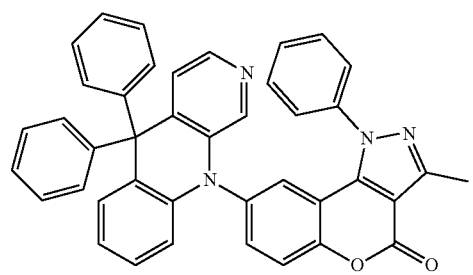

Compound 7
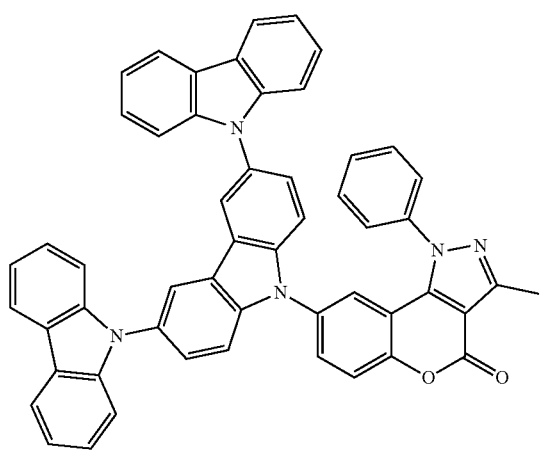
Compound 10
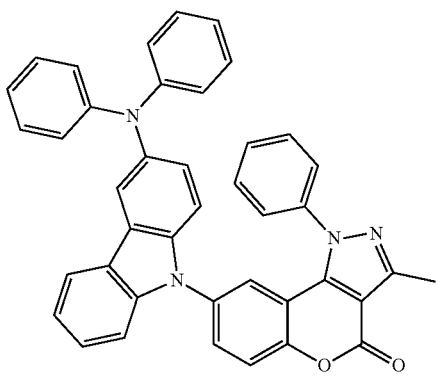
Compound 8
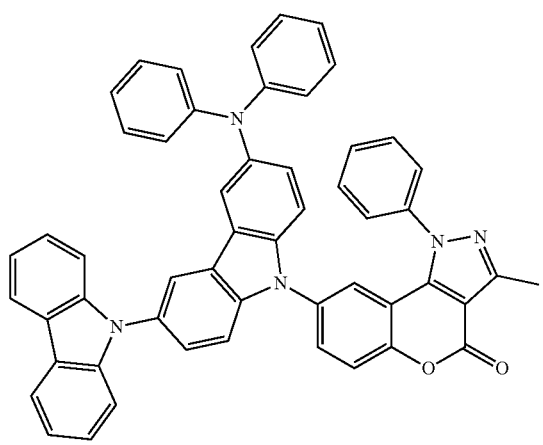
Compound 11
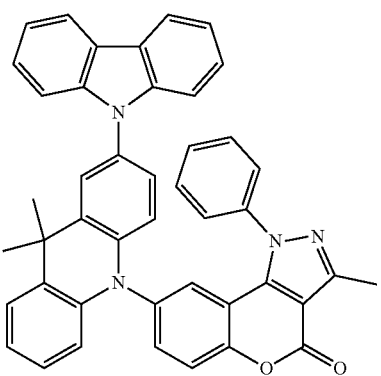
Compound 9
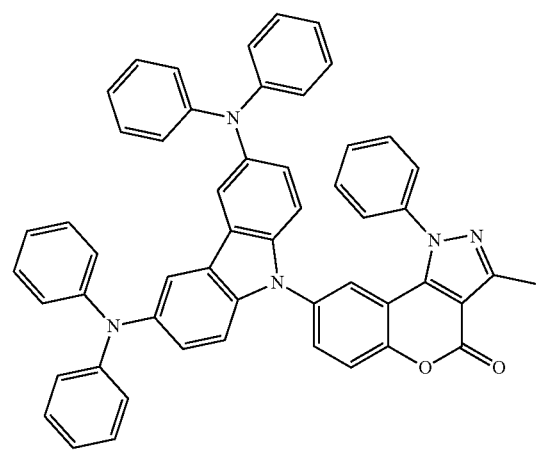
Compound 12
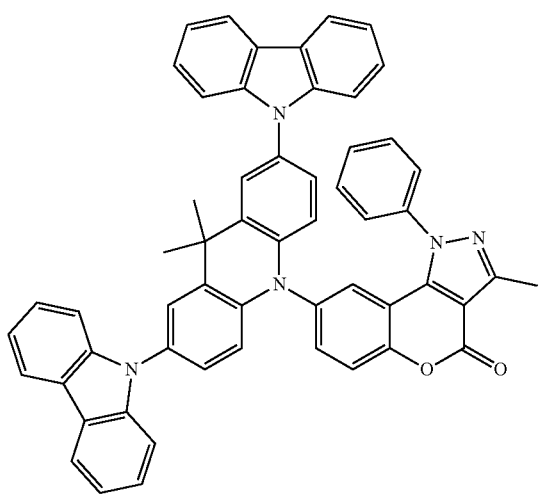

Compound 13
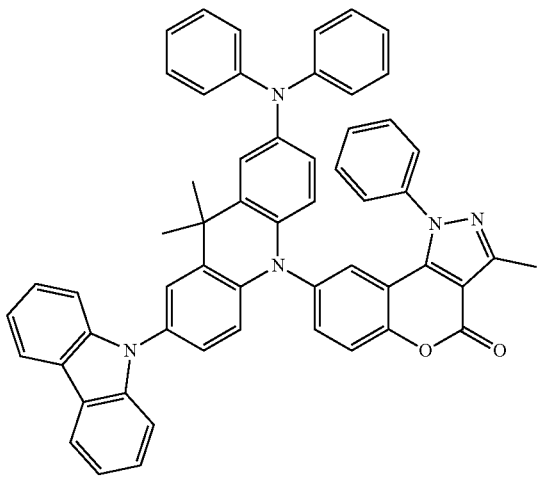
Compound 14
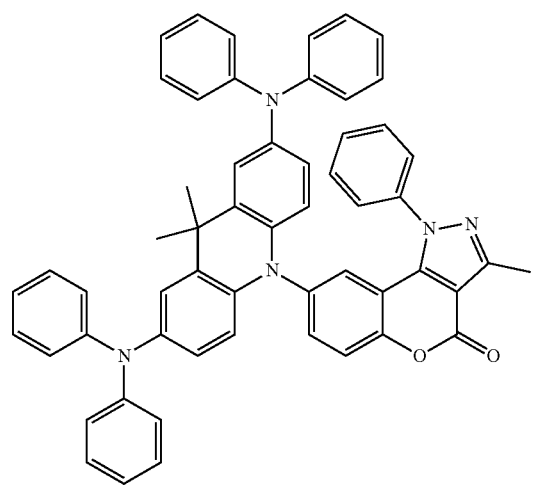
Compound 15
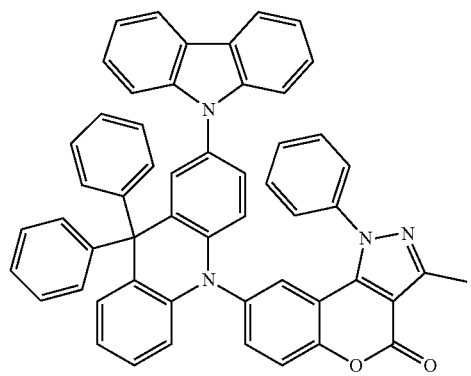
Compound 16
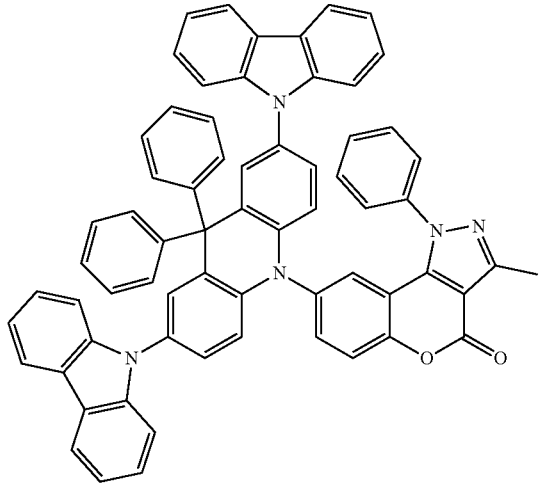
Compound 17
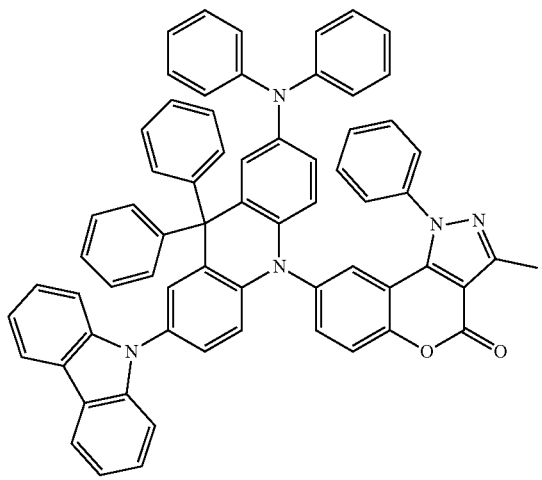
Compound 18
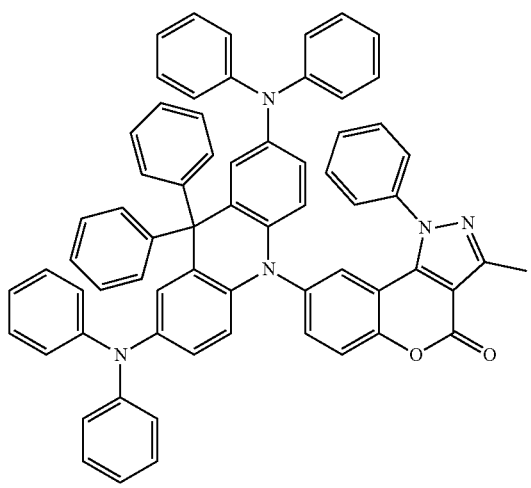

Compound 19
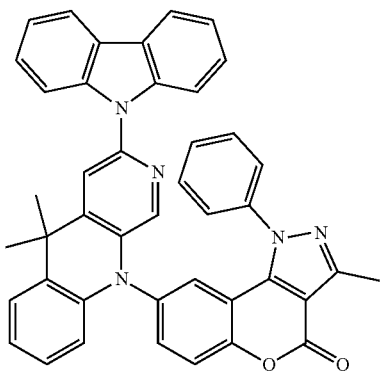
Compound 22
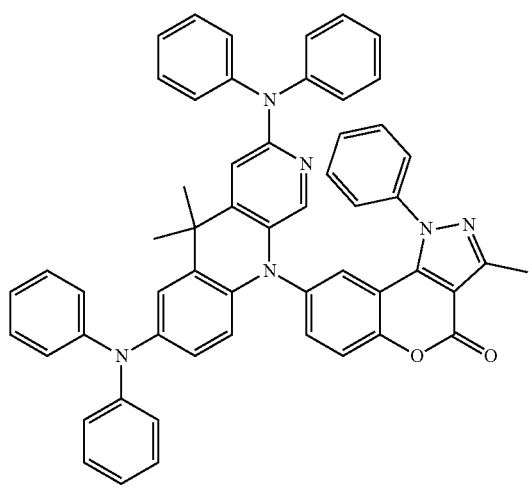
Compound 20
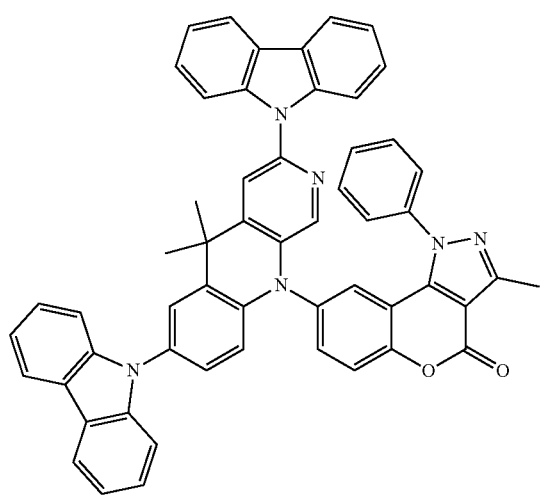
Compound 23
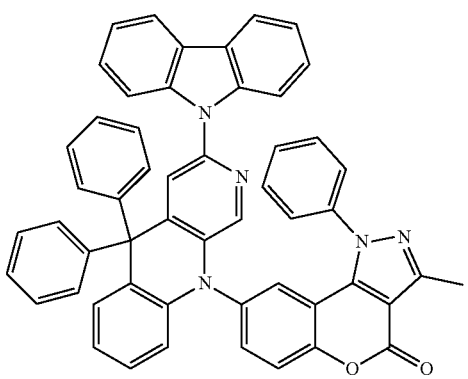
Compound 21
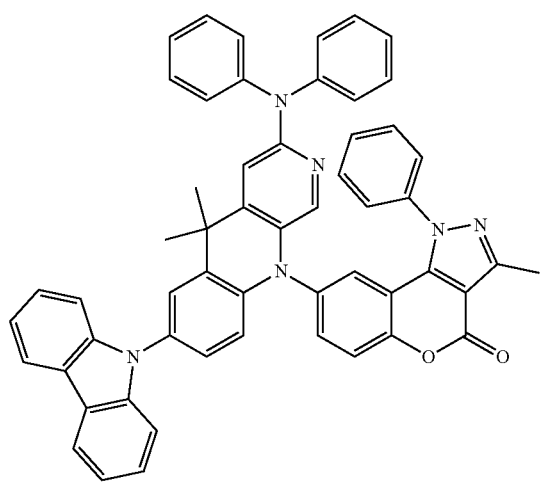
Compound 24
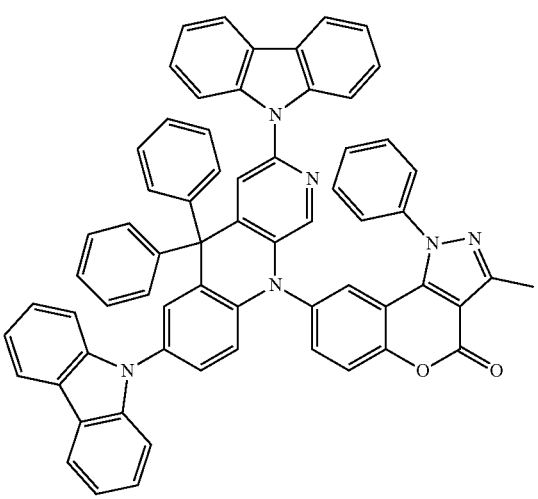

-continued

Compound 25

Compound 26

4. An organic light emitting diode, comprising:
a first electrode;
a second electrode,
   wherein the second electrode faces the first electrode; and
a first emitting material layer,
   wherein the first emitting material layer is disposed between the first and second electrodes, and
   wherein the first emitting material layer comprises an organic compound of Formula 1:

[Formula 1]

wherein Ar1 is a heteroaryl group including a nitrogen atom, and Ar2 is a $C_6$ to $C_{30}$ aryl group, and
wherein R is a $C_1$ to $C_{10}$ alkyl group.

5. The organic light emitting diode according to claim 4, wherein the organic compound is a first host, and the first emitting material layer further comprises a delayed fluorescent compound as a first dopant.

6. The organic light emitting diode according to claim 5, wherein an energy level of a triplet state of the first host is greater than an energy level of a triplet state of the first dopant.

7. The organic light emitting diode according to claim 5, wherein a difference between an energy level of a HOMO of the first host and an energy level of a HOMO of the first dopant or a difference between an energy level of a LUMO of the first host and an energy level of a LUMO of the first dopant is less than 0.5 eV.

8. The organic light emitting diode according to claim 5, wherein the first emitting material layer further comprises a fluorescent compound as a second dopant, and an energy level of a singlet state of the first dopant is greater than an energy level of a singlet state of the second dopant.

9. The organic light emitting diode according to claim 8, wherein an energy level of a triplet state of the first dopant is smaller than an energy level of a triplet state of the first host and greater than an energy level of the triplet state of a second dopant.

10. The organic light emitting diode according to claim 5, further comprising:
   a second emitting material layer comprising a second host and a fluorescent compound as a second dopant,
   wherein the second emitting material layer is positioned between the first electrode and the first emitting material layer.

11. The organic light emitting diode according to claim 10, further comprising:
   an electron blocking layer between the first electrode and the second emitting material layer,
   wherein the second host is the same as a material of the electron blocking layer.

12. The organic light emitting diode according to claim 10, further comprising:
   a third emitting material layer including a third host and a fluorescent compound as a third dopant,
   wherein the third emitting material layer is positioned between the second electrode and the first emitting material layer.

13. The organic light emitting diode according to claim 12, further comprising:
   a hole blocking layer between the second electrode and the third emitting material layer,
   wherein the third host is the same as a material of the hole blocking layer.

14. The organic light emitting diode according to claim 12, wherein an energy level of the singlet state of the first dopant is greater than each of an energy level of the singlet state of the second dopant and an energy level of the singlet state of the third dopant.

15. The organic light emitting diode according to claim 12, wherein an energy level of the singlet state and an energy level of the triplet state of the first host is greater than an energy level of the singlet state and an energy level of the triplet state of the first dopant, respectively, and
   wherein an energy level of the singlet state of the second host is greater than an energy level of the singlet state of the second dopant, and an energy level of the singlet state of the third host is greater than an energy level of the singlet state of the third dopant.

16. The organic light emitting diode according to claim 10, wherein an energy level of the singlet state of the first dopant is greater than an energy level of the singlet state of the second dopant.

17. The organic light emitting diode according to claim 4, wherein Ar1 is selected from Formula 2:

[Formula 2]

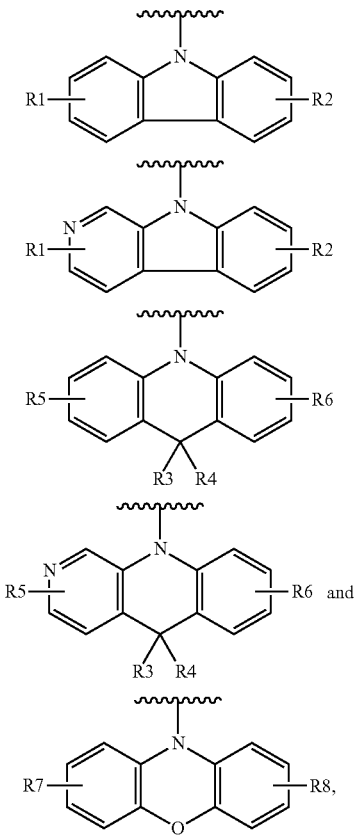

wherein each of R1, R2 and R5 to R8 is independently selected from the group consisting of hydrogen, carbazolyl and arylamine group, and wherein each of R3 and R4 is independently selected from the group consisting of $C_1$ to $C_{10}$ alkyl and $C_6$ to $C_{30}$ aryl, or $R_3$ and $R_4$ form a fused-ring.

18. The organic light emitting diode according to claim 4, wherein the organic compound is selected from the group consisting of:

Compound 1

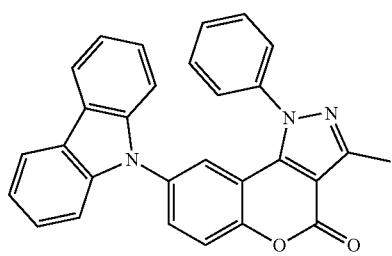

-continued

Compound 2

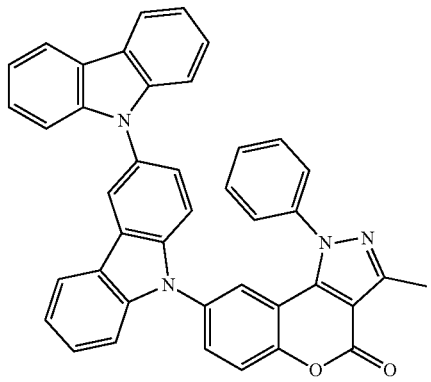

Compound 3

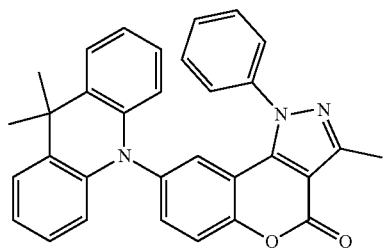

Compound 4

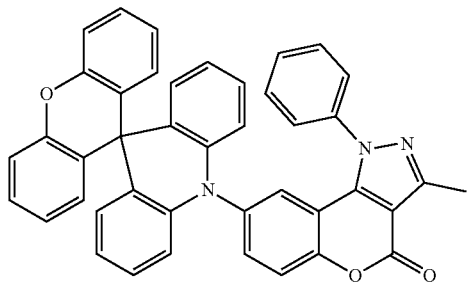

Compound 5

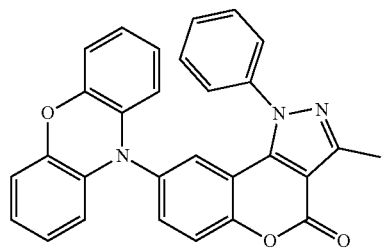

Compound 6

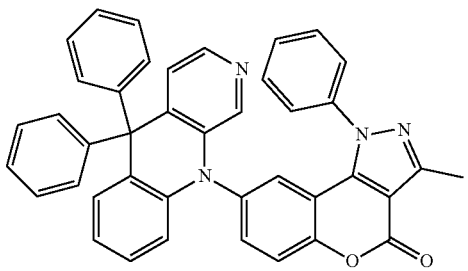

Compound 7
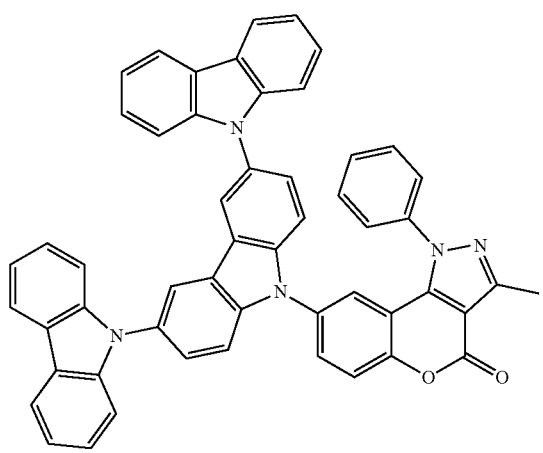
Compound 8
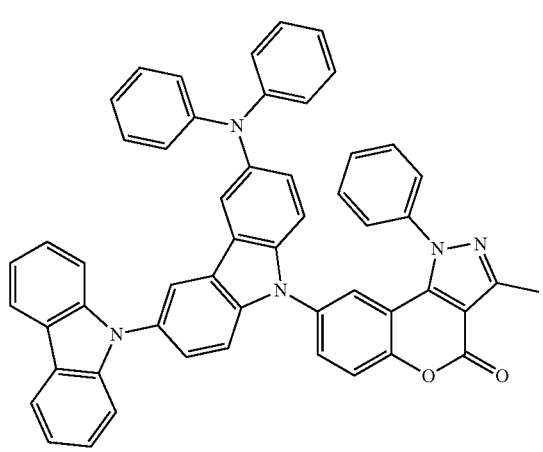
Compound 9
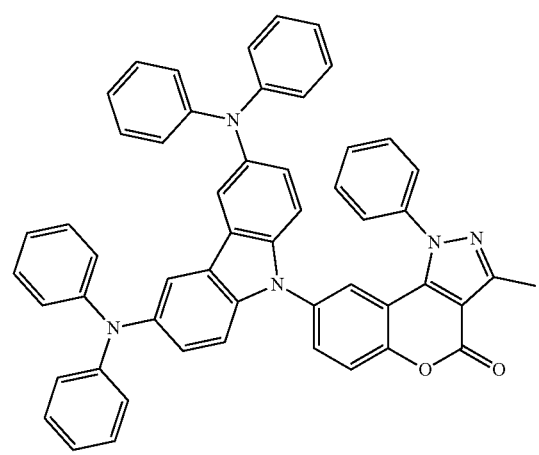
Compound 10
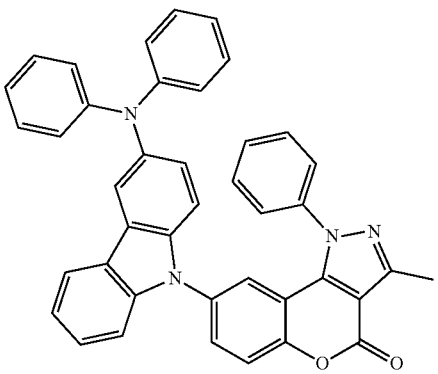
Compound 11
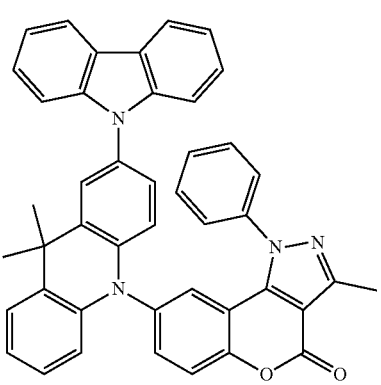
Compound 12
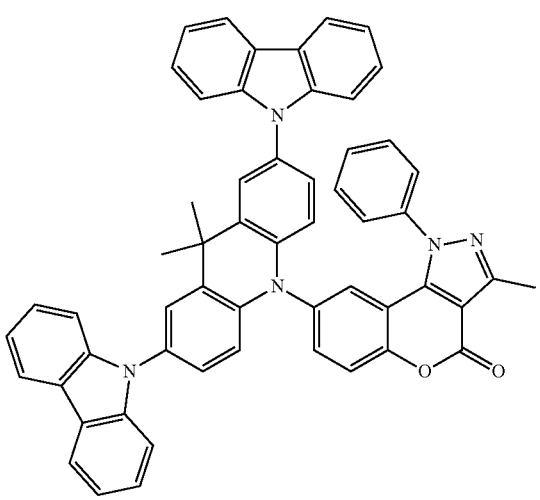

Compound 13
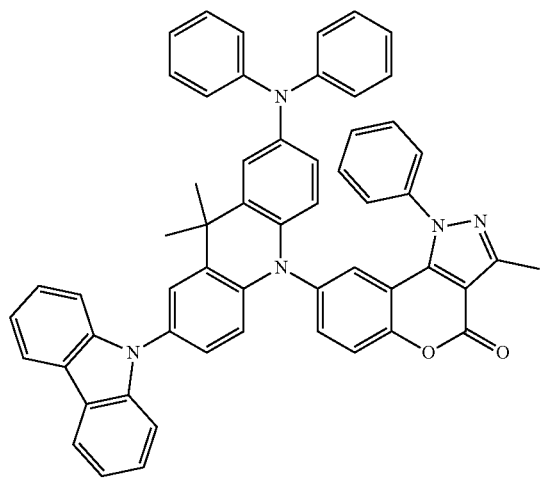
Compound 14
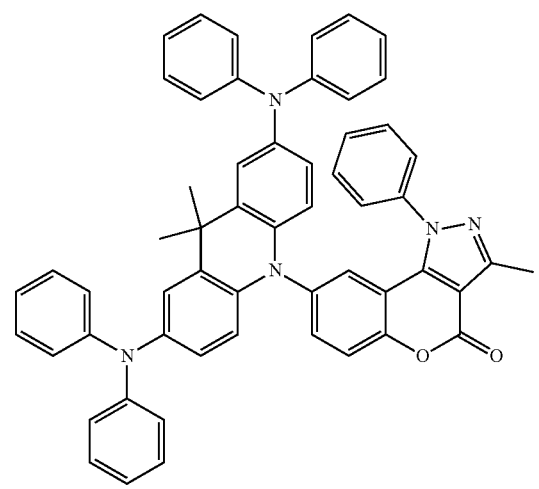
Compound 15
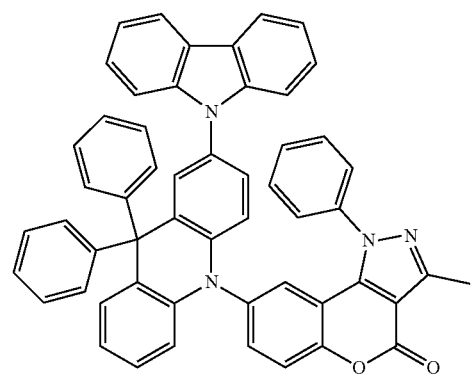
Compound 16
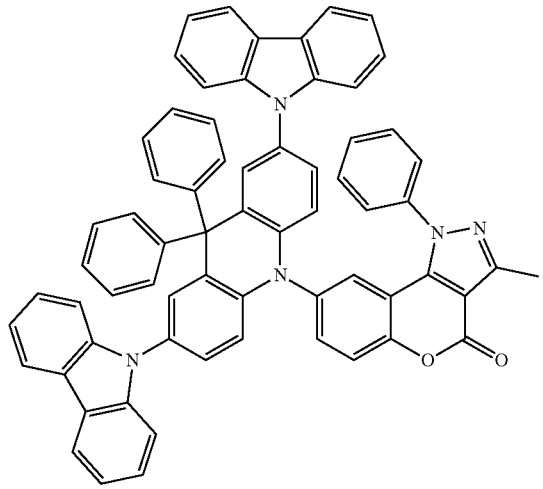
Compound 17
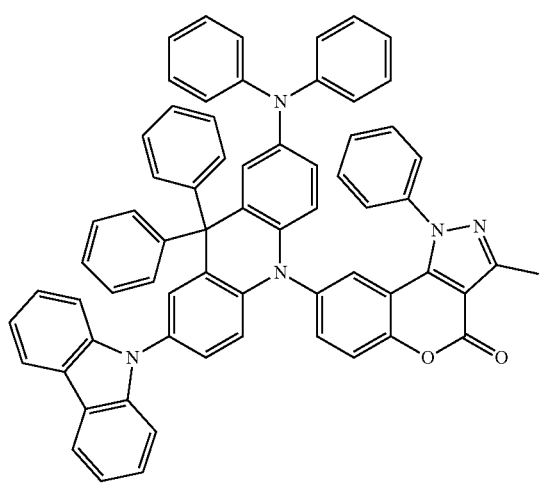
Compound 18
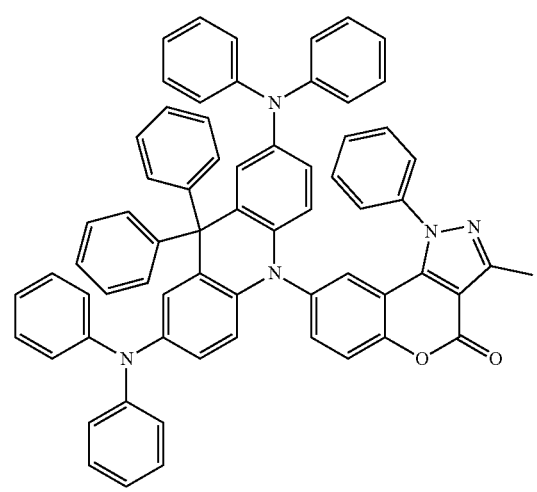

Compound 19
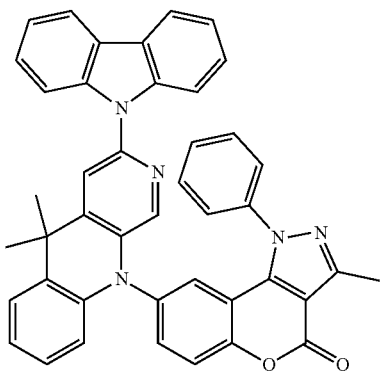
Compound 20
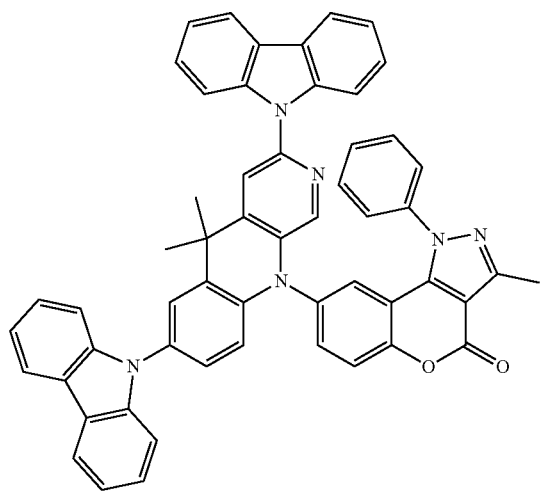
Compound 21
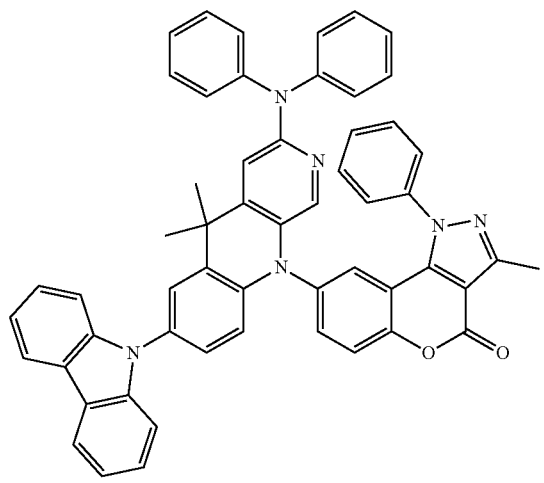
Compound 22
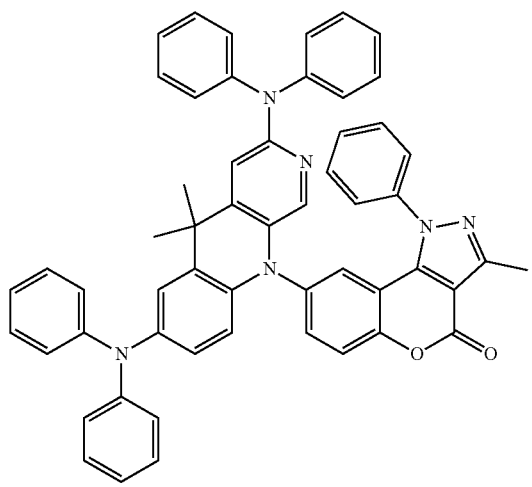
Compound 23
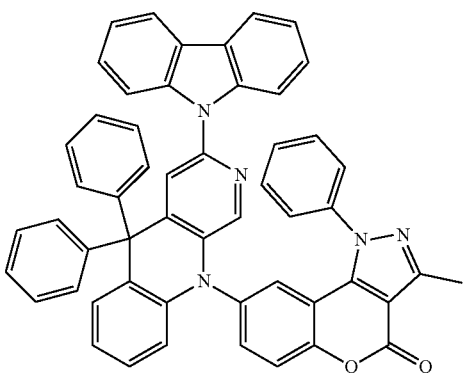
Compound 24
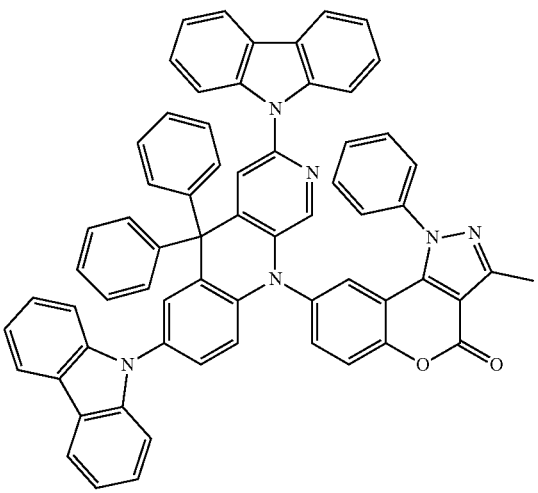

Compound 25

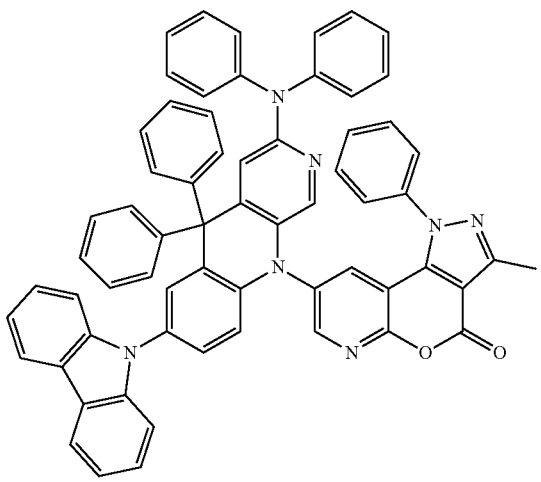

Compound 26

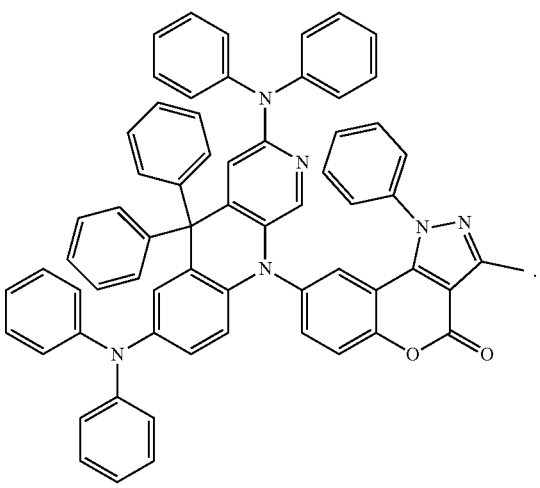

19. An organic light emitting display device, comprising:
a substrate;
an organic light emitting diode disposed on the substrate, the organic light emitting diode comprising:
 a first electrode;
 a second electrode facing the first electrode; and
 an emitting material layer between the first electrode and second electrode; and
a thin film transistor positioned between the substrate and the organic light emitting diode and connected to the organic light emitting diode,
wherein the emitting material layer comprises an organic compound with a structure of Formula 1:

[Formula 1]

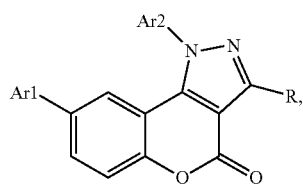

wherein Ar1 is a heteroaryl group including nitrogen atom, and Ar2 is a $C_6$ to $C_{30}$ aryl group, and
wherein R is a $C_1$ to $C_{10}$ alkyl group.

20. The organic light emitting display device according to claim 19, wherein the organic compound is selected from the group consisting of:

Compound 1

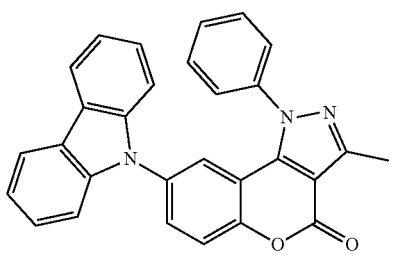

Compound 2

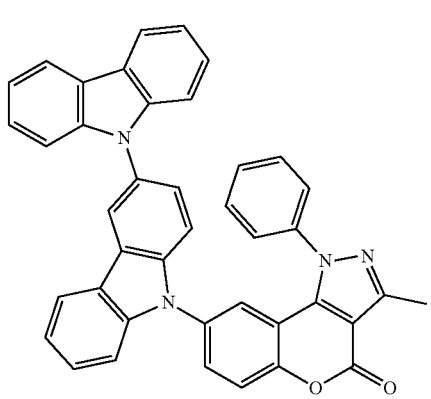

Compound 3

Compound 4

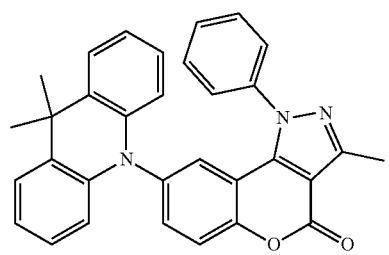

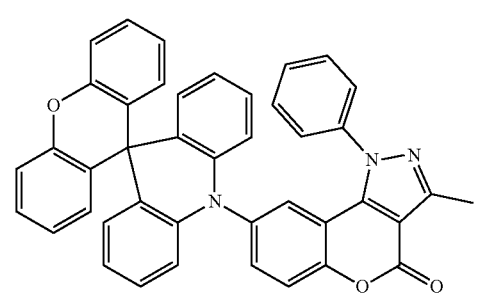

Compound 5
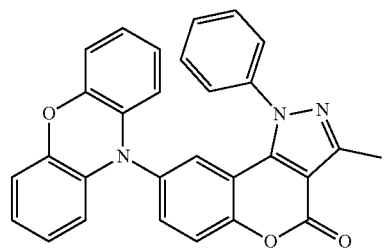
Compound 6
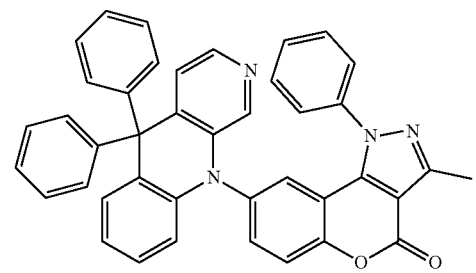
Compound 7
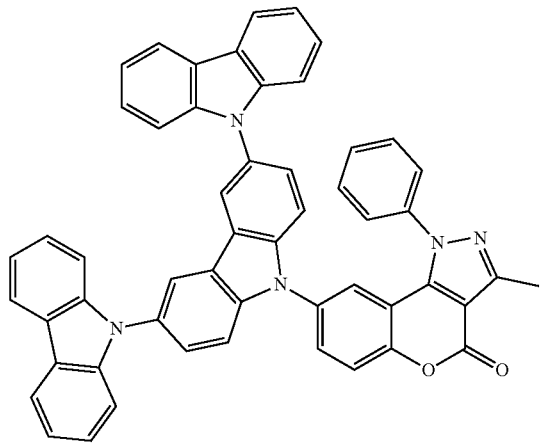
Compound 8
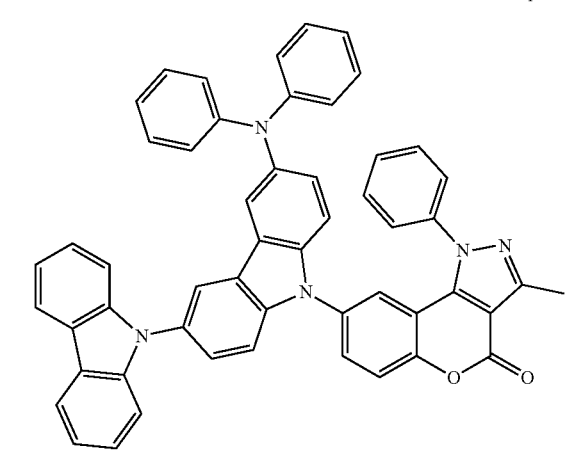
Compound 9
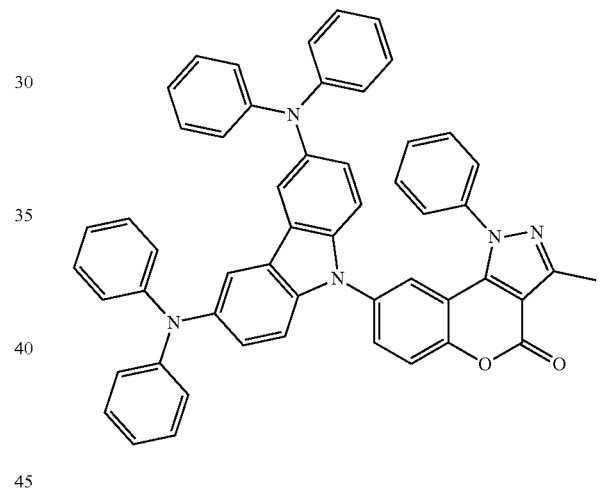
Compound 10
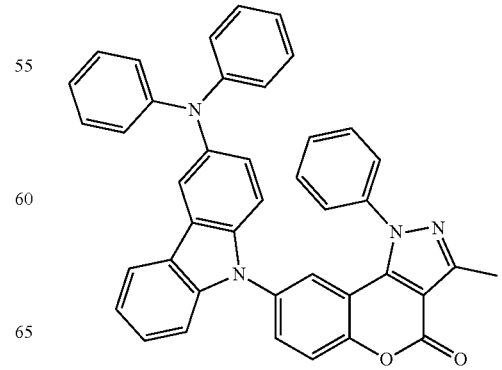

Compound 11
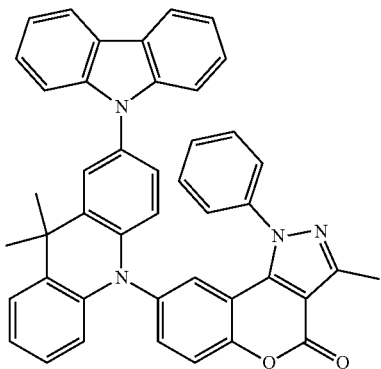
Compound 14
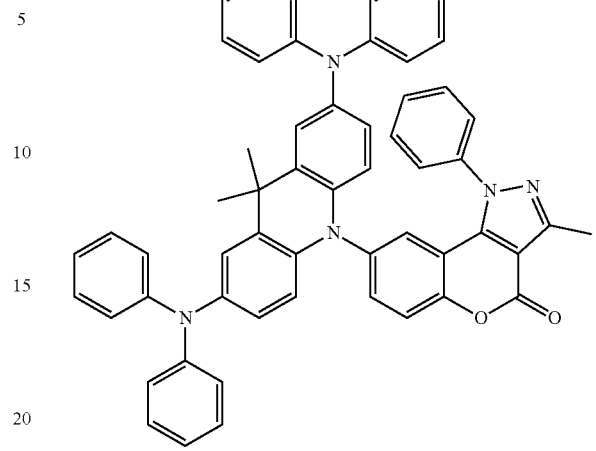
Compound 12
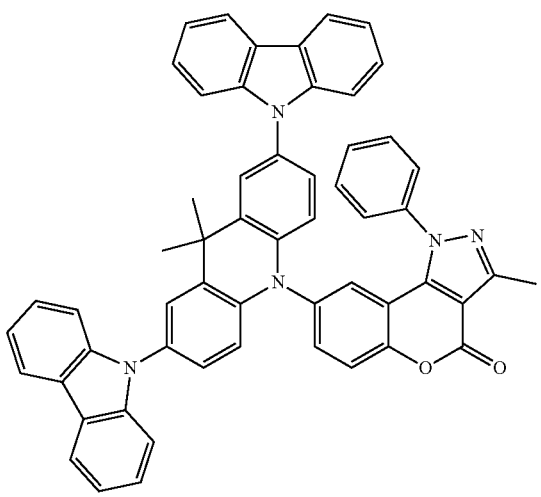
Compound 15
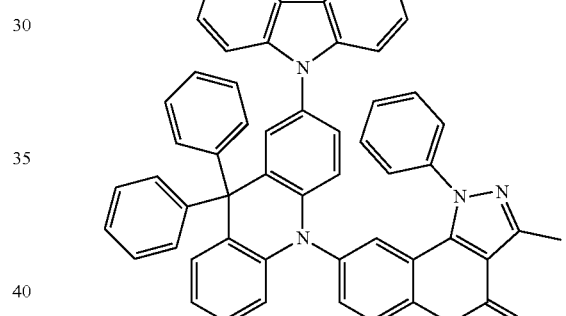
Compound 13
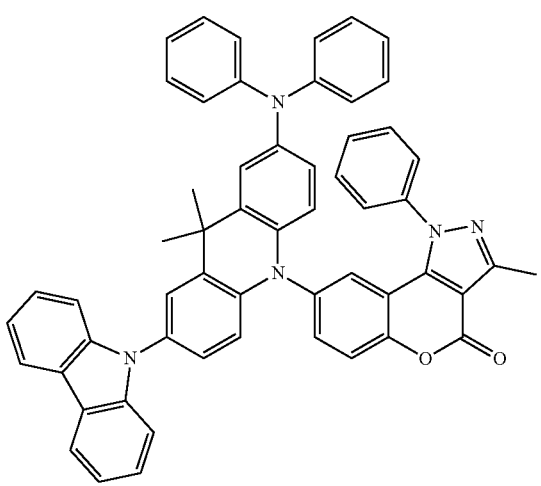
Compound 16
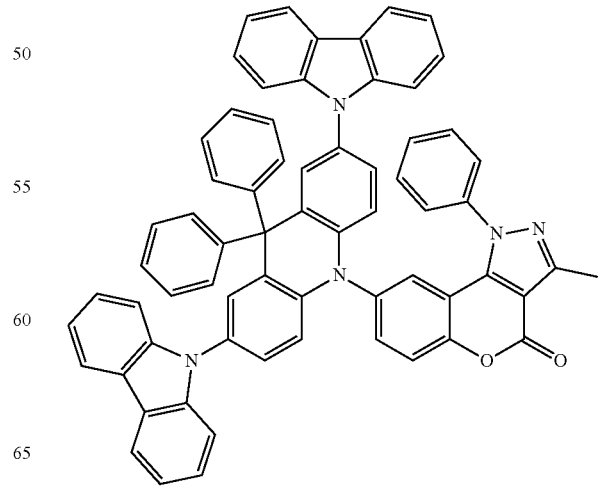

Compound 17
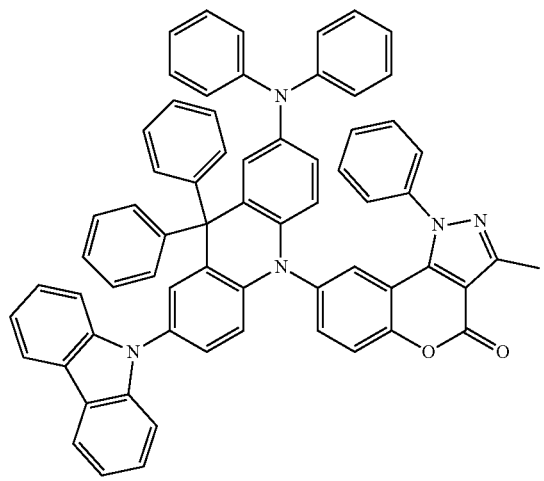
Compound 18
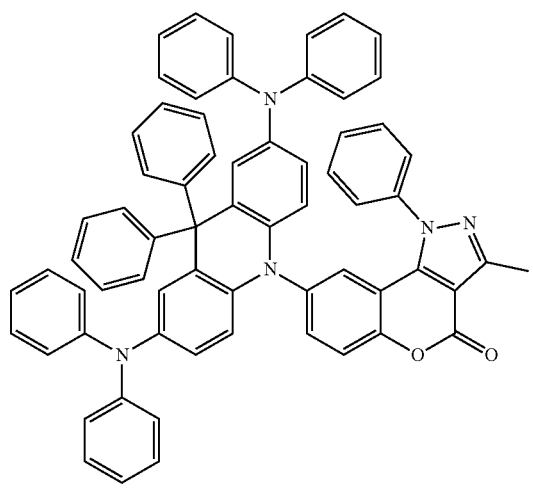
Compound 19
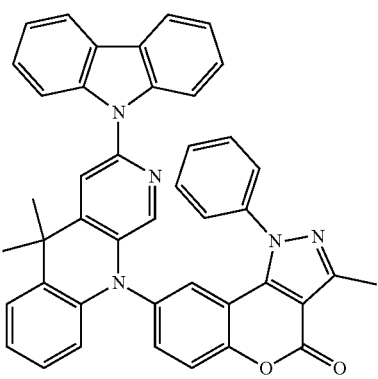
Compound 20
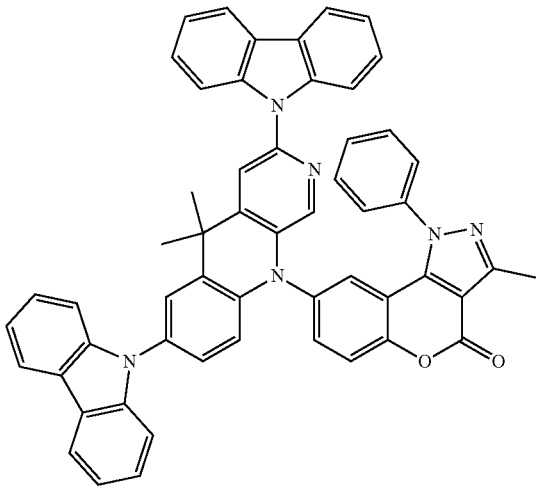
Compound 21
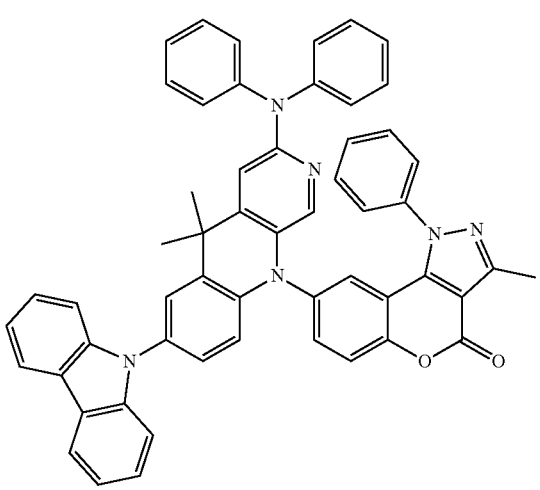
Compound 22
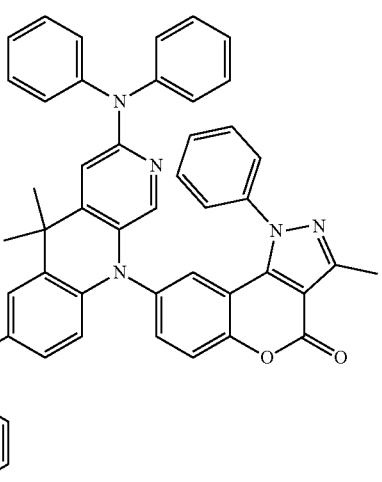

-continued
Compound 23
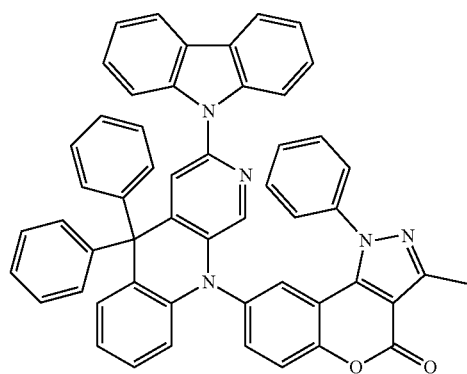
Compound 24
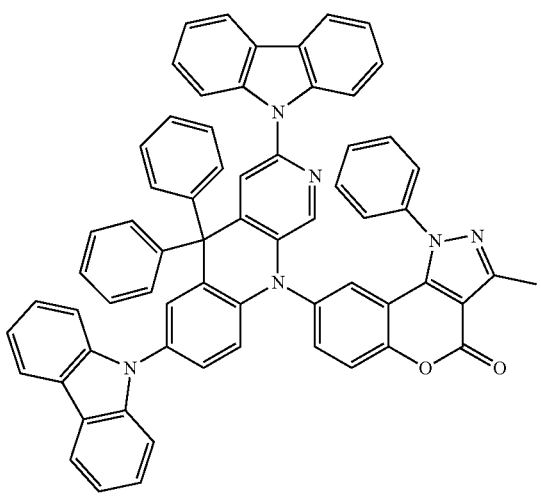
Compound 25
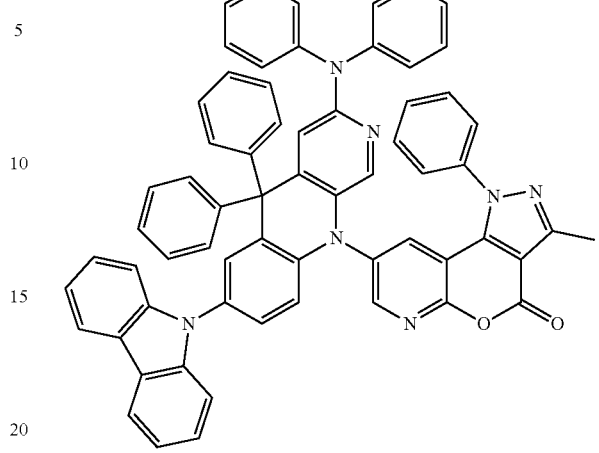
Compound 26
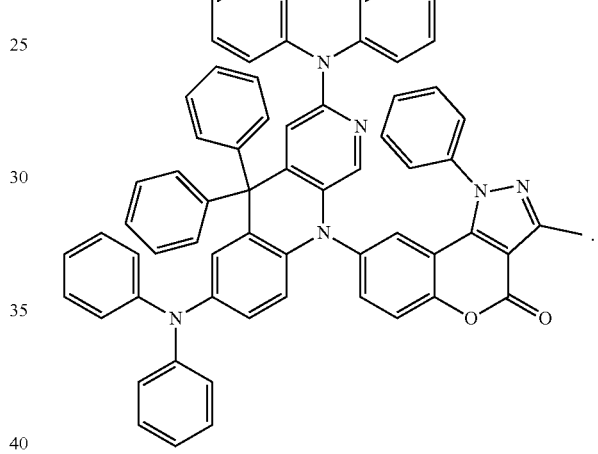
* * * * *